United States Patent
Pappalardo

(10) Patent No.: US 9,138,772 B2
(45) Date of Patent: Sep. 22, 2015

(54) DISPENSING ASSEMBLY AND METHOD USING SNAP ENGAGEMENT OF A MIXER AND A CARTRIDGE

(71) Applicant: Nordson Corporation, Westlake, OH (US)

(72) Inventor: Matthew E. Pappalardo, Ewing, NJ (US)

(73) Assignee: Nordson Corporation, Westlake, OH (US)

( * ) Notice: Subject to any disclaimer, the term of this patent is extended or adjusted under 35 U.S.C. 154(b) by 0 days.

(21) Appl. No.: 13/664,512

(22) Filed: Oct. 31, 2012

(65) Prior Publication Data

US 2014/0117044 A1    May 1, 2014

(51) Int. Cl.
*B67D 7/78* (2010.01)
*B05C 17/005* (2006.01)

(52) U.S. Cl.
CPC ..... *B05C 17/00506* (2013.01); *B05C 17/00553* (2013.01)

(58) Field of Classification Search
CPC ............ B05C 17/00506; B05C 17/00509; B05C 17/00503; B05C 17/00516; B05C 17/00563; B05C 17/00566
USPC ...... 222/145.5, 153.14, 137, 145.1; 220/784, 326, 319, 320, 321; 215/209, 215/216, 225, 290, 274, 275
See application file for complete search history.

(56) References Cited

U.S. PATENT DOCUMENTS

| D167,725 S | 9/1952 | Soffer |
| 2,681,463 A | 6/1954 | Mayor |
| D199,606 S | 11/1964 | Waterman |
| D204,103 S | 3/1966 | Lydon |
| 3,499,574 A * | 3/1970 | Yates, Jr. ............ 220/784 |
| D225,838 S | 1/1973 | Filder |
| D242,327 S | 11/1976 | Schneider |

(Continued)

FOREIGN PATENT DOCUMENTS

| DE | 202006004738 U1 | 6/2006 |
| DE | 202006004738 U1 * | 7/2006 |

(Continued)

OTHER PUBLICATIONS

DE 202006004738—English Translation (Machine Translation).*

(Continued)

*Primary Examiner* — J. Casimer Jacyna
*Assistant Examiner* — Benjamin R Shaw
(74) *Attorney, Agent, or Firm* — Wood, Herron & Evans, LLP

(57) ABSTRACT

A dispensing assembly includes a cartridge for containing a fluid and a mixer for mixing and dispensing the fluid. The cartridge includes a locking flange or wall and the mixer includes a locking latch configured to snap into and out of engagement with the locking flange. To this end, the mixer and the cartridge are coupled and uncoupled by a snap-on and snap-off engagement that does not require relative rotation of the mixer and the cartridge. The locking latch also includes a latch release mechanism such as a squeeze handle, a peel handle, or a locking ring for forcing the locking latch into and out of engagement with the locking flange. As a result, the connection of the mixer and the cartridge is a quick and easy process and cross contamination of fluids in multiple fluid cartridges is avoided.

18 Claims, 22 Drawing Sheets

(56) References Cited

U.S. PATENT DOCUMENTS

| | | | |
|---|---|---|---|
| 4,022,352 A * | 5/1977 | Pehr | 222/153.14 |
| D262,149 S | 12/1981 | Plaut | |
| D286,380 S | 10/1986 | Harman | |
| D318,233 S | 7/1991 | Ackerman | |
| D328,244 S | 7/1992 | Hamilton et al. | |
| D332,221 S | 1/1993 | Willems | |
| D335,809 S | 5/1993 | Reifenberger | |
| 5,228,599 A | 7/1993 | Keller | |
| D358,295 S | 5/1995 | Moench | |
| D358,329 S | 5/1995 | Dickie | |
| 5,462,204 A | 10/1995 | Finn | |
| 5,918,772 A | 7/1999 | Keller et al. | |
| 6,186,363 B1 | 2/2001 | Keller et al. | |
| D440,654 S | 4/2001 | Mark | |
| D462,268 S | 9/2002 | Schroeder et al. | |
| D471,797 S | 3/2003 | Guerrera et al. | |
| D485,577 S | 1/2004 | Lord et al. | |
| 6,769,574 B1 | 8/2004 | Keller | |
| 7,316,330 B2 | 1/2008 | Muller et al. | |
| 7,367,475 B2 | 5/2008 | Horth et al. | |
| 7,481,333 B2 | 1/2009 | Goldberg et al. | |
| 7,631,782 B2 | 12/2009 | Engelbrecht et al. | |
| 7,717,357 B2 | 5/2010 | Gantenbein et al. | |
| D633,384 S | 3/2011 | Tanaka | |
| 8,100,295 B2 * | 1/2012 | Keller | 222/137 |
| D659,244 S | 5/2012 | Hermle | |
| D660,695 S | 5/2012 | Ishizawa et al. | |
| D661,598 S | 6/2012 | Battisti | |
| 2004/0150223 A1 * | 8/2004 | Campau | 285/308 |
| 2005/0035153 A1 | 2/2005 | Brown | |
| 2005/0230422 A1 | 10/2005 | Muller et al. | |
| 2006/0157508 A1 | 7/2006 | Suchan et al. | |
| 2008/0083782 A1 | 4/2008 | Heusser et al. | |
| 2010/0102088 A1 * | 4/2010 | Keller | 222/137 |
| 2010/0102477 A1 | 4/2010 | Helie et al. | |
| 2010/0206905 A1 | 8/2010 | Horner et al. | |
| 2011/0121035 A1 | 5/2011 | Greter et al. | |

FOREIGN PATENT DOCUMENTS

| | | |
|---|---|---|
| DE | 202011002407 U1 | 4/2011 |
| EP | 2145599 A1 | 1/2010 |
| EP | 2407249 A1 | 1/2012 |
| EP | 2468416 A1 | 6/2012 |
| GB | 2357448 A | 6/2001 |

OTHER PUBLICATIONS

European Patent Office, European Search Report in EP Appilcation No. 13190447, Feb. 3, 2014.

* cited by examiner

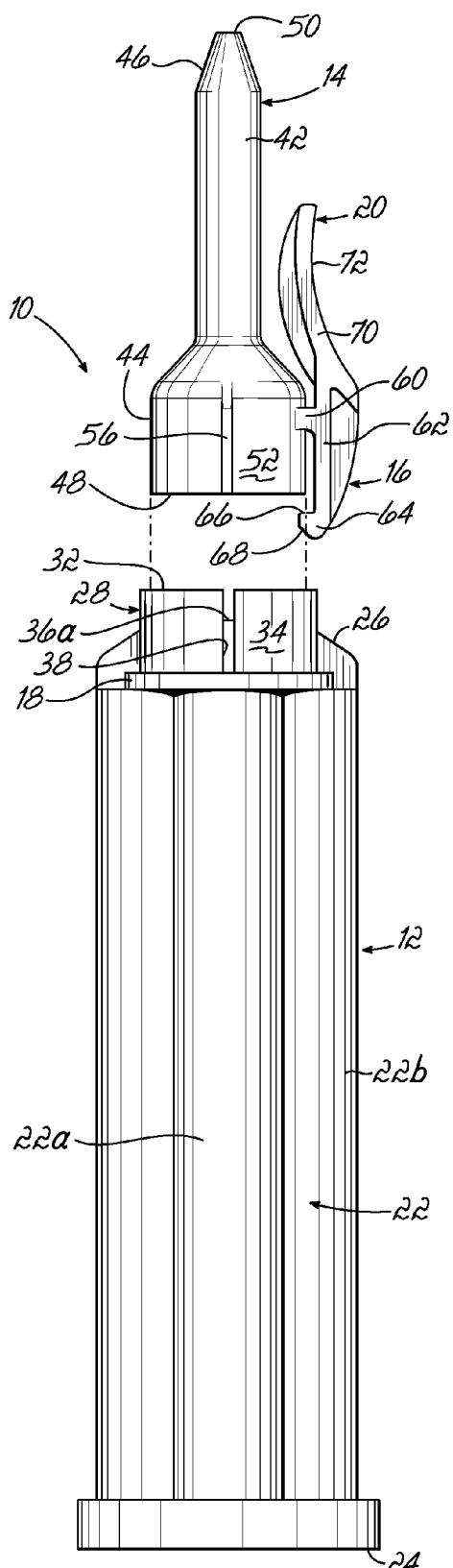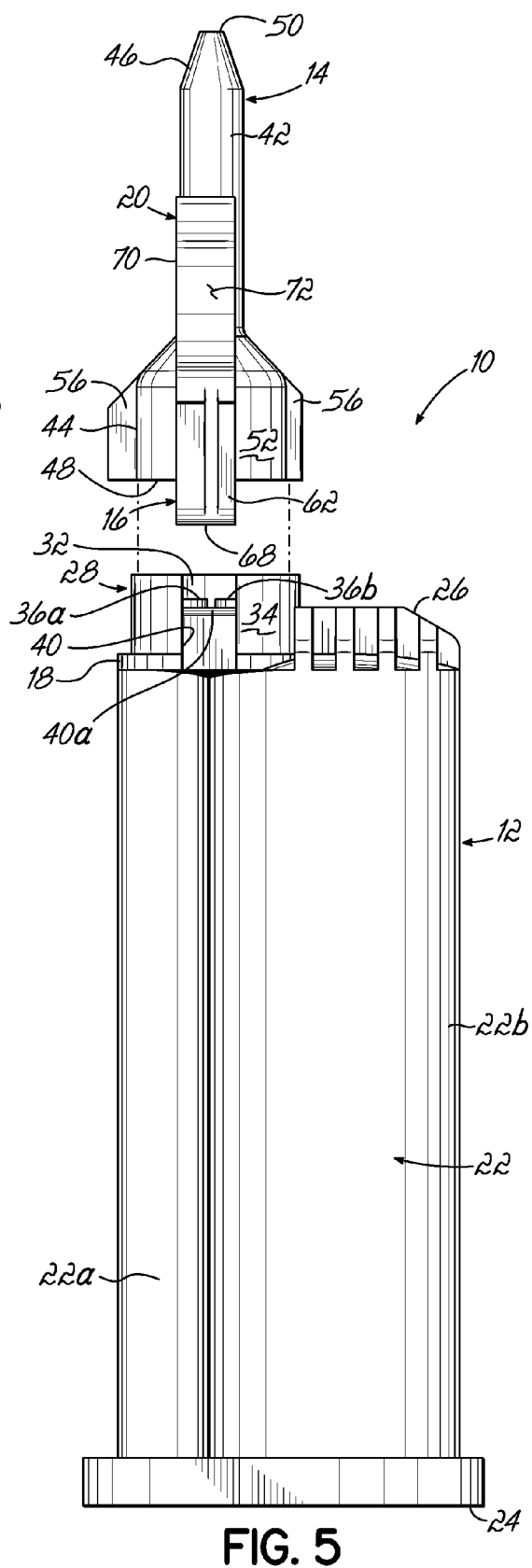

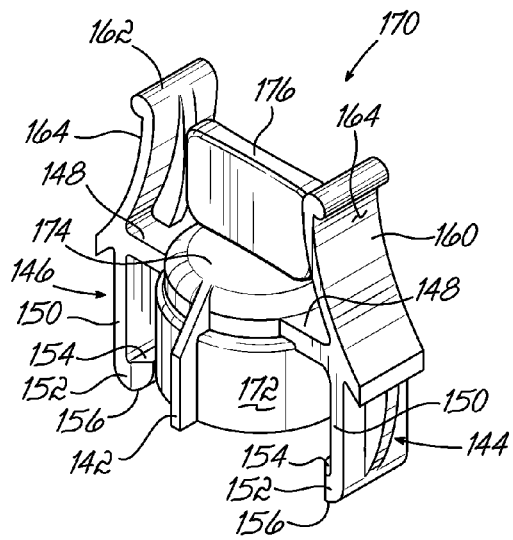 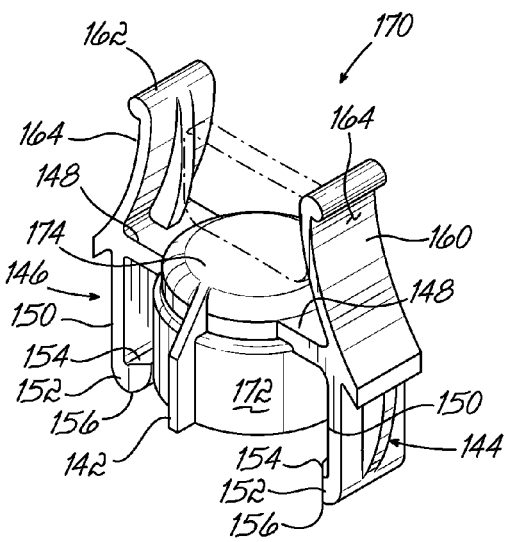
FIG. 16A　　　　FIG. 16B
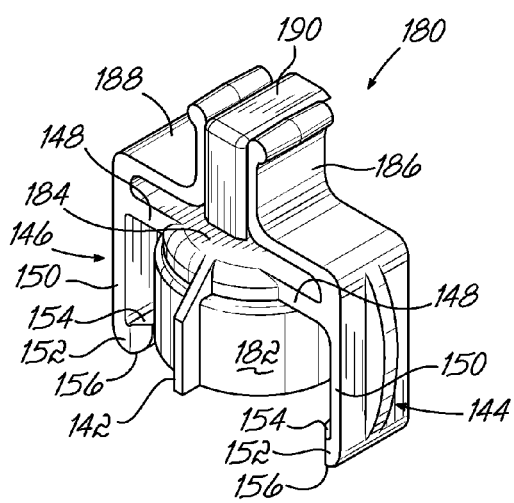 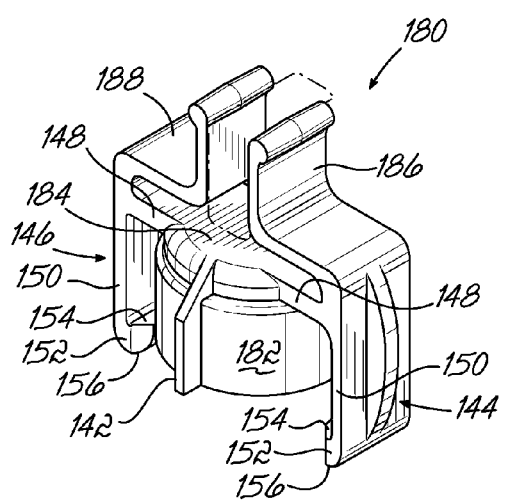
FIG. 17A　　　　FIG. 17B

DISPENSING ASSEMBLY AND METHOD USING SNAP ENGAGEMENT OF A MIXER AND A CARTRIDGE

FIELD OF THE INVENTION

The present invention generally relates to a dispensing assembly and method and, more particularly, to components of a mixer and a cartridge configured to retain these elements in engagement together during dispensing.

BACKGROUND

In the dispensing field, it is common to manufacture and ship cartridges holding the fluid to be dispensed and static mixers separately. There are a number of reasons for this separate shipping, including, but not limited to, the excessive length of some mixer/cartridge combinations and the potential use of a plurality of different mixers with a cartridge. Consequently, the mixers and cartridges need to be provided with corresponding connection members that may sealingly couple the mixer to an outlet of the cartridge and enable removal of the mixer from the cartridge after use. Moreover, many known cartridges include separated outlets for delivering two or more fluids into the mixer to be mixed before dispensing. As a result, the connection members for these mixers and cartridges must also be configured to properly orient inlets on the mixer with the outlets on the cartridge (i.e., "coding"), while avoiding cross contamination of fluids across the multiple outlets.

Generally, two types of connection members have been used in the art, and especially in the field of so-called double cartridges or multiple cartridges. The first known type of connection member includes bayonet-style tabs on one component and corresponding L-shaped slots on the other component. One example of such a connection arrangement is shown in U.S. Pat. No. 6,186,363 to Keller et al. The rotary locking and unlocking movement required to use this type of bayonet connection may lead to the transport and cross contamination of one fluid from a first outlet of the cartridge to another fluid in the second outlet of the cartridge. If the fluids being mixed together from the cartridge react with one another, as is typical in these dispensing systems, then this cross contamination may eventually carry this reaction into the fluid chamber of the cartridge itself, leading to blockage of one or both of the outlets. Furthermore, the bayonet-style tabs must generally be formed with a very small size, which limits the structural strength and rigidity possible to counteract ever increasing backpressures formed when using smaller diameter mixers.

The second known type of connection member includes a threaded ring on the mixer that engages with a threaded boss on the cartridge. One example of this type of connection arrangement is shown in U.S. Pat. No. 5,228,599 to Keller. These threaded components are difficult to manufacture reliably with the tight tolerances required to ensure a viable seal between the mixer and the cartridge. Additionally, these threaded components generally require multiple rotations of the threaded ring to engage the mixer with the cartridge. As a result, the installation and removal process for each mixer is an inefficient and time-consuming process.

Thus, it would be desirable to address some of the drawbacks associated with known connection members used to removably connect a mixer and a cartridge in a dispensing apparatus or a dispensing method.

SUMMARY OF THE INVENTION

According to one embodiment of the invention, a dispensing assembly includes a cartridge for containing a fluid and a mixer for mixing and dispensing the fluid. The cartridge includes a fluid chamber and an outlet socket in communication with the fluid chamber. The outlet socket defines a proximal wall and a hollow port extending distally from the proximal wall. The mixer includes a mixer conduit, an inlet socket sized to be engaged with the hollow port and in fluid communication with the mixer conduit, and a first locking latch extending outwardly from the inlet socket. The first locking latch is configured to snap into engagement with the proximal wall to couple the cartridge to the mixer. The dispensing assembly also includes a latch release mechanism coupled to the first locking latch and operable to disengage the first locking latch from the proximal wall without rotating the mixer with respect to the cartridge.

Consequently, the dispensing apparatus of this embodiment enables quick and reliable attachment and removal of the mixer and the cartridge. In one aspect of the invention, one of the inlet socket or the outlet socket includes a radial projection, while the other of the inlet socket and the outlet socket includes a radial slot. The radial slot receives the radial projection when the mixer and cartridge are coupled together. To this end, the radial slot and the radial projection engage one another to properly orient the mixer with respect to the cartridge and also to prevent relative rotation of the mixer and the cartridge during engagement. The radial projection and the first locking latch may be provided in a non-symmetrical arrangement to ensure proper alignment of the mixer to the cartridge.

In another aspect according to the invention, the latch release mechanism includes a first squeeze handle extending distally from the first locking latch towards the mixer conduit. The first squeeze handle is configured to be depressed towards the mixer conduit to snap the first locking latch out of engagement with the proximal wall. Additionally, the mixer may also include a second locking latch positioned on an opposite side of the inlet socket from the first locking latch. In these instances, the latch release mechanism includes a second squeeze handle coupled to the second locking latch and extending distally from the second locking latch towards the mixer conduit. Thus, the first and second squeeze handles may be squeezed toward one another to release the snap connection of the first and second locking latches on the proximal wall.

In a related aspect having first and second locking latches, the latch release mechanism may also include a locking ring engaged with the first and second locking latches. The locking ring is moveable along the first and second locking latches from a locked position to an unlocked position. In the locked position, the locking ring compresses the first and second locking latches to prevent disengagement of these locking latches from the proximal wall. The first and second locking latches may also include retention projections for engaging corresponding detents on the locking ring in either the locked position or the unlocked position. In this regard, the locking ring can prevent unintentional disconnection of the mixer from the cartridge.

In another aspect of the invention, the latch release mechanism includes a first peel handle extending proximally from the first locking latch toward the fluid chamber. The first peel handle is configured to be pulled away from the fluid chamber to peel the first locking latch in the same direction out of engagement with the proximal wall. Similar to the embodiments with a squeeze handle, the mixer of this aspect may include a second locking latch on an opposing side from the first locking latch, the second locking latch optionally including a second peel handle.

In yet another aspect of the invention, the mixer includes first and second locking latches positioned on opposite sides of the mixer, and the latch release mechanism includes a locking ring engaged with the first and second locking latches. The locking ring is moveable along the first and second locking latches between a locked position in which the locking ring compresses the first and second locking latches to an unlocked position in which the first and second locking latches may be disengaged from the proximal wall. To this end, the first and second locking latches may be biased away from the proximal wall when the locking ring is moved to the unlocked position to automatically disengage the first and second locking latches from the proximal wall. Alternatively, or in addition, the first and second locking latches include retention projections and the locking ring includes corresponding detents for engaging the retention projections at either the locked position or the unlocked position.

In a further aspect of the invention, the mixer includes a plurality of locking latches that extend outwardly from the inlet socket to substantially surround the proximal wall. The latch release mechanism in this aspect includes a locking ring engaged with the plurality of locking latches and moveable along the plurality of locking latches between a locked position and an unlocked position. Similar to the locking rings described above, this locking ring compresses the plurality of locking latches to prevent disengagement of the mixer from the cartridge, and the plurality of locking latches may be biased away from the proximal wall when the locking ring moves to the unlocked position. The inlet socket may also include a plurality of outwardly directed projections, and the locking ring may include an exterior handle and an interior slot configured to receive one of the outwardly directed projections. To this end, the exterior handle may be aligned in one of various desired orientations relative to the cartridge and the mixer.

In yet another aspect of the invention, the dispensing assembly further includes a sealing cap configured to engage the cartridge to close the outlet socket when the mixer is disengaged from the cartridge. The sealing cap includes first and second locking latches configured to snap into engagement with the proximal wall and first and second squeeze handles coupled to the first and second locking latches. The first and second squeeze handles are configured to be depressed toward one another to snap the first and second locking latches out of engagement with the proximal wall. The sealing cap also includes a blocking member coupled to the first and second squeeze handles and located between the first and second squeeze handles. The blocking member prevents unintentional depression of the first and second squeeze handles toward one another until the blocking member is removed from the sealing cap.

In another aspect of the invention, the outlet socket includes a generally annular wall interrupted by a locking notch, and the first locking latch includes a base extending radially outwardly from the inlet socket and an arm coupled to the base for snapping into engagement with the proximal wall. The base is sized to fit within the locking notch in the outlet socket. The locking notch may also include a ramp surface, and the arm may include a locking tab with a leading surface that is chamfered or rounded. The ramp surface and the leading surface cooperate to assist with snapping the first locking latch into engagement with the proximal wall.

In another embodiment of the invention, a method of mixing and dispensing a fluid contained within a cartridge includes connecting a mixer having a mixer conduit and an inlet socket to the cartridge by aligning the inlet socket with an outlet socket of the cartridge. The method also includes snapping a first locking latch positioned on the inlet socket into engagement with a locking flange positioned on the outlet socket. Fluid is then dispensed from a fluid chamber in the cartridge through the mixer conduit and out of the mixer. The method further includes disengaging the mixer from the cartridge by disengaging the first locking latch from the locking flange without rotating the mixer with respect to the cartridge.

In one aspect, the first locking latch includes a first squeeze handle that is depressed toward the mixer to force the first locking latch to move in an opposite direction away from the locking flange. In another aspect, the first locking latch is a first peel handle that is pulled away from the cartridge to force the first locking latch to move in the same direction away from the locking flange. The method may further include snapping a sealing cap into engagement with the outlet socket of the cartridge after disengaging the mixer from the cartridge. The sealing cap is configured to block further flow of the fluid out of the fluid chamber while the mixer is not coupled to the cartridge.

These and other objects and advantages of the invention will become more readily apparent during the following detailed description taken in conjunction with the drawings herein.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

FIG. 4 is a side view of the dispensing assembly of FIG. 1 with the mixer disengaged from the cartridge and showing a first locking latch on the mixer with a first squeeze handle extending from the first locking latch;

FIG. 5 is a front view of the dispensing assembly of FIG. 1 with the mixer disengaged from the cartridge;

FIG. 16A is a perspective view of a sealing cap configured for use with the cartridge of FIG. 13, the sealing cap including first and second squeeze handles and a blocking member;

FIG. 16B is a perspective view of the sealing cap of FIG. 16A, showing the blocking member removed;

FIG. 17A is a perspective view of another sealing cap configured for use with the cartridge of FIG. 13, the sealing cap including first and second squeeze handles and a blocking member;

FIG. 17B is a perspective view of the sealing cap of FIG. 17A, showing the blocking member removed;

DETAILED DESCRIPTION OF THE ILLUSTRATIVE EMBODIMENTS

Figure 1:
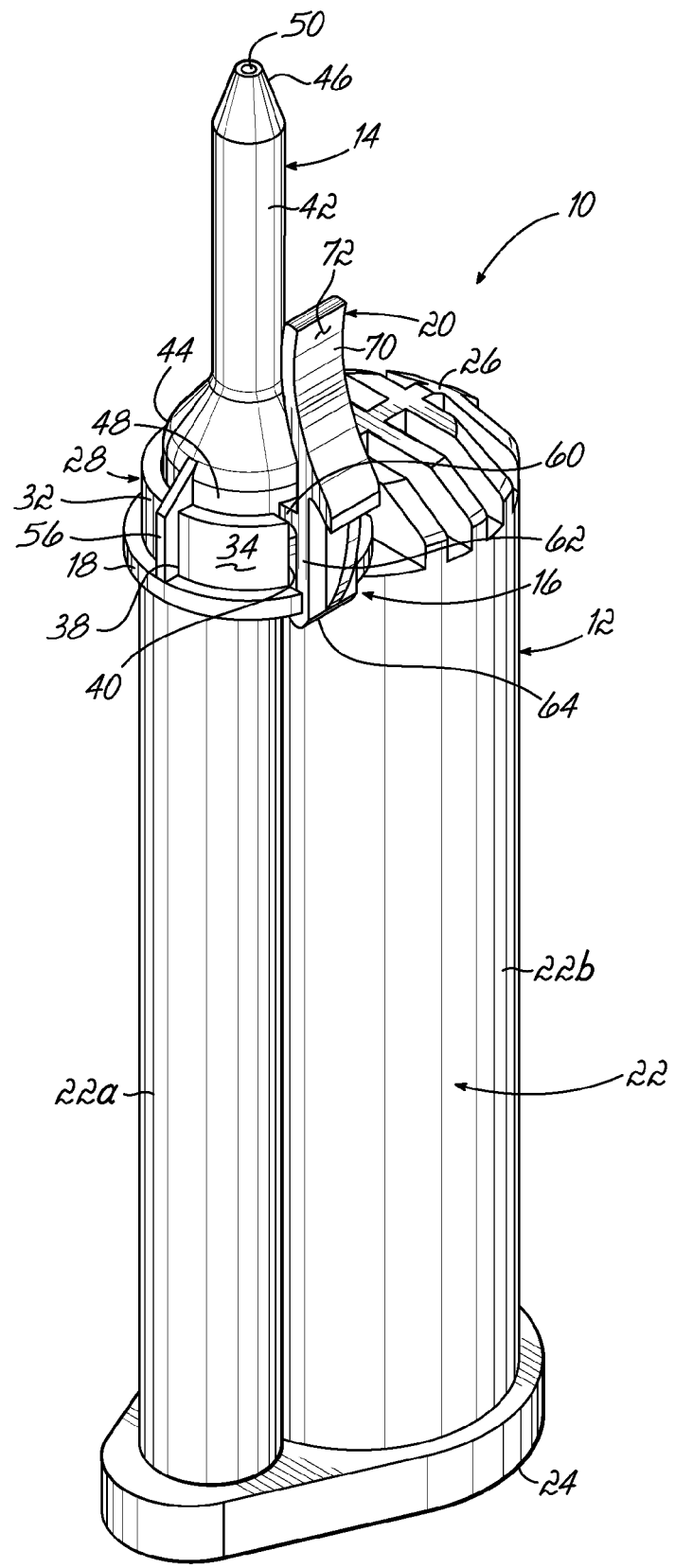
FIG. 1 is a perspective view of a dispensing assembly with a snap engagement between the mixer and the cartridge according to one embodiment of the current invention.

Referring to FIGS. 1-6B, a first embodiment of a dispensing assembly 10 in accordance with the principles of the current invention is shown. Generally speaking, the dispensing assembly 10 includes a cartridge 12 for containing a fluid to be dispensed and a mixer 14 in the form of a static mixer 14 configured to mix and dispense the fluid in the cartridge 12. As a result of the lengths of each of these elements 12, 14 and the desire to use different mixers 14 with the same cartridge 12 (and vice versa), the cartridge 12 and the mixer 14 are manufactured and shipped separately and then must be assembled before a dispensing operation. Advantageously, the mixer 14 includes a first locking latch 16 operable to snap into and out of engagement with a corresponding flange or wall on the cartridge 12. In the first embodiment of FIGS. 1-6, for example, the first locking latch 16 extends from the mixer 14 and is configured to snap into and out of engagement with a proximal wall 18 defined on the cartridge 12. As a result of the snap engagement of the cartridge 12 and the mixer 14, these components may be attached and removed from one another quickly and easily with a simple squeezing, pulling, and/or sliding movement of a latch release mechanism 20 coupled to the first locking latch 16. Furthermore, the cartridge 12 and the mixer 14 may be coupled and uncoupled without rotating the mixer 14 with respect to the cartridge 12, which avoids cross contamination of fluids when the cartridge 12 contains two or more fluids to be mixed and dispensed. Thus, the dispensing assembly 10 of this and other embodiments described below overcomes many of the drawbacks associated with known threaded or bayonet-style connection members in this field.

With specific reference to FIGS. 1-5, the cartridge 12 and the mixer 14 of the dispensing assembly 10 of this embodiment are shown in further detail. In this regard, the mixer 14 is shown coupled to the cartridge 12 in FIG. 1 and uncoupled from the cartridge 12 in FIGS. 2-5. The cartridge 12 includes a fluid chamber 22 extending from a proximal end 24 to a distal end 26. The fluid chamber 22 of this embodiment includes two fluid chamber portions 22a, 22b adjacent to one another for containing two fluids to be mixed together before dispensing (e.g., two reactive components that mix to form an adhesive material). Although the two fluid chamber portions 22a, 22b are shown with differing sizes in FIG. 1, it will be understood that the fluid chamber portions 22a, 22b may be resized relative to one another in other embodiments consistent with the invention. Moreover, the fluid chamber 22 may include more or fewer fluid chamber portions in other embodiments without departing from the invention. As well understood in the dispensing field, the proximal end 24 of the cartridge 12 is configured to receive an actuator (not shown) such as a pneumatically or mechanically actuated piston for pushing the fluids out of the fluid chamber 22 and into the mixer 14 when the mixer 14 is coupled to the cartridge 12. The distal end 26 of the cartridge 12 includes an outlet socket 28 for connecting to the mixer 14 as described in further detail below.

Figure 2:
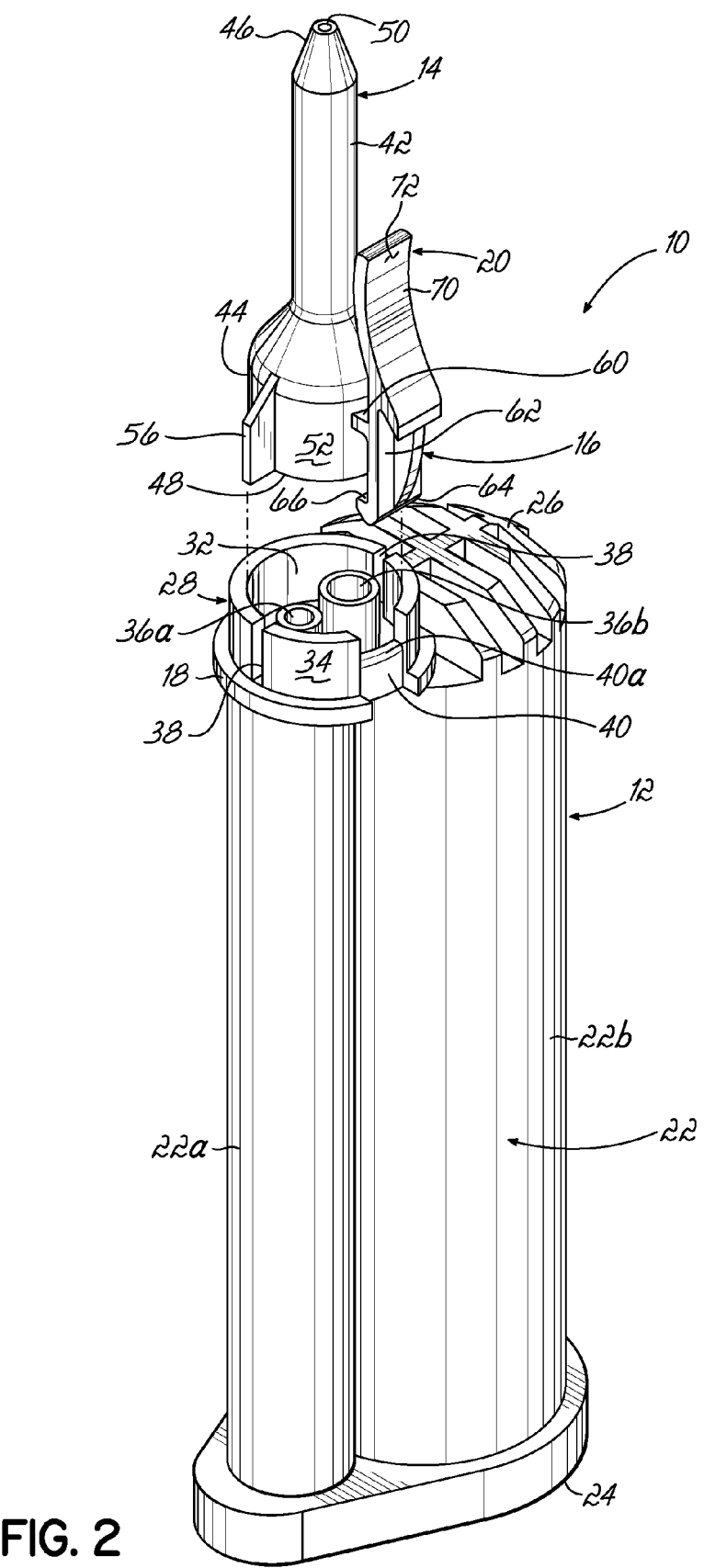
FIG. 2 is a perspective view of the dispensing assembly of FIG. 1 with the mixer disengaged from the cartridge.

The outlet socket 28 of the cartridge 12 is shown in further detail in FIG. 2. In this regard, the outlet socket 28 includes the proximal wall 18 (also referred to as a proximal flange) and a hollow port 32 extending distally from the proximal wall 18. The hollow port 32 is formed by a generally annular wall 34 substantially surrounding first and second fluid outlets 36a, 36b extending through the proximal wall 18. The first and second fluid outlets 36a, 36b communicate with the corresponding fluid chamber portions 22a, 22b and may be coded with different cross-sectional sizes as shown. Alternatively, the first and second fluid outlets 36a, 36b could be formed with the same cross-sectional size in other embodiments of the dispensing assembly 10. The generally annular wall 34 is uninterrupted about the periphery of the hollow port 32 except at two opposing radial slots 38 formed in the annular wall 34 and at a locking notch 40 collectively formed in the annular wall 34 and the proximal wall 18. The radial slots 38 and the locking notch 40 are configured to receive corresponding structure on the mixer 14, including the first locking latch 16, as described in further detail below. Although the hollow port 32 is shown with slightly smaller size than the proximal wall 18, it will be understood that the hollow port 32 could be resized to be the same size as the proximal wall 18 in other embodiments consistent with the invention.

Figure 3:
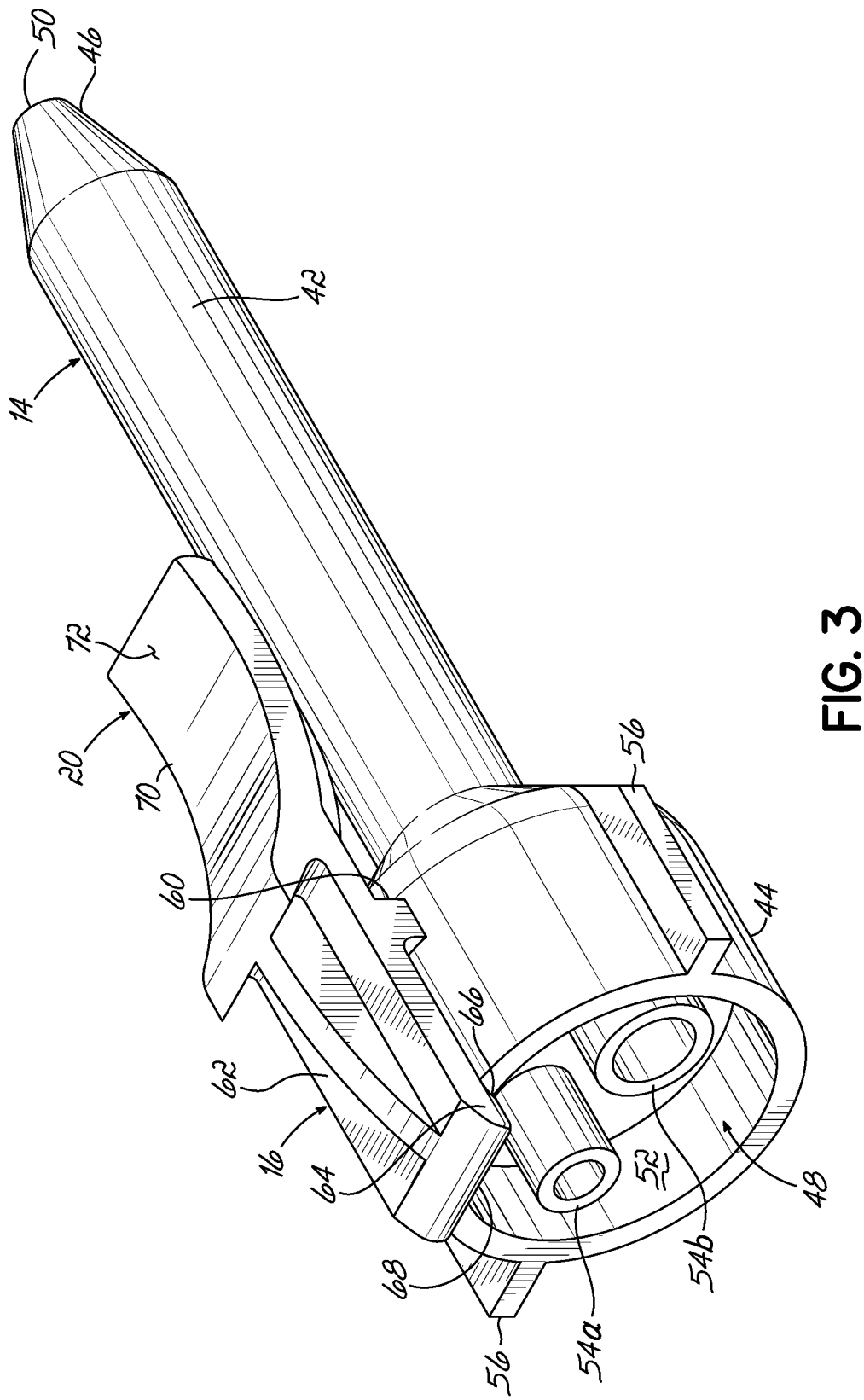
FIG. 3 is a perspective view of the mixer used with the dispensing assembly of FIG. 1, with the mixer flipped in orientation to illustrate details of an inlet socket of the mixer.

The mixer 14 is shown in further detail in FIG. 3. More specifically, the mixer 14 includes a mixer conduit 42 extending from a proximal end 44 to a distal end 46. The mixer conduit 42 generally includes one or more known mixing baffles (not shown) of various types for rotating and combining one or more fluids together as the fluid(s) traverse the length of the mixer conduit 42. The mixer 14 also includes an inlet socket 48 located at the proximal end 44 of the mixer conduit 42 and a dispensing outlet 50 (see FIGS. 1 and 2) at the distal end 46 of the mixer conduit 42. The inlet socket 48 defines a generally annular shape and is sized to be inserted into the hollow port 32 to thereby be engaged with the outlet socket 28. In this regard, the inlet socket 48 includes an annular wall 52 surrounding two fluid inlets 54a, 54b sized to correspond to the two fluid outlets 36a, 36b of the outlet socket 28. Thus, the separated fluid inlets 54a, 54b and fluid outlets 36a, 36b keep the first and second fluids separated until their intended combination within the mixer conduit 42. The annular wall 52 defines a slightly smaller diameter than the corresponding annular wall 34 of the outlet socket 28 such that the inlet socket 48 is inserted into the hollow port 32 in the illustrated embodiment; however, it will be understood that the annular wall 52 could be reconfigured to surround the annular wall 34 of the outlet socket 28 in other embodiments.

As briefly noted above, the mixer 14 includes corresponding structure for interaction with the radial slots 38 and the locking notch 40 of the outlet socket 28. As shown in FIG. 3, the inlet socket 48 includes two opposing radial projections 56 extending outwardly from the annular wall 52. The radial projections 56 are positioned and sized to slide into the radial slots 38 of the outlet socket 28 when the mixer 14 is coupled to the cartridge 12. The first locking latch 16 also extends outwardly from the annular wall 52 and is configured to snap into engagement with the cartridge 12 by sliding over the locking notch 40.

More particularly, the first locking latch 16 includes a base 60 projecting radially outward from the annular wall 52 and an arm 62 extending in a proximal direction from the base 60 generally parallel to and beyond the annular wall 52 as shown in FIGS. 3-5. The base 60 is advantageously formed to project from only a portion of the annular wall 52 such that the base 60 can fit within the locking notch 40 when the mixer 12 is coupled to the cartridge 14. A locking tab 64 is positioned on a free end of the arm 62 opposite the base 60 and projects radially inwardly from the arm 62. The locking tab 64 is configured to snap over a shoulder defined by the proximal wall 18 at the locking notch 40. Although the locking tab 64 is formed with an oblique trailing surface 66 to snugly engage or abut the proximal wall 18, the leading surface 68 of the locking tab 64 may be chamfered or rounded as shown to facilitate movement of the locking tab 64 and the arm 62 over the locking notch 40. Similarly, the locking notch 40 may also be chamfered or rounded to define a ramp surface 40a to assist with this movement of the first locking latch 16. Therefore, the leading surface 68 and the ramp surface 40a cooperate to help the first locking latch 16 slide over the locking notch 40 to engage the proximal wall 18. The precise appearance and contour defined by the base 60, the arm 62, and the locking tab 64 may be modified in other embodiments without departing from the scope of the current invention.

The latch release mechanism 20 is further shown in FIGS. 3-5. The latch release mechanism 20 of this embodiment includes a first squeeze handle 70 connected to the first locking latch 16 adjacent the base 60 and extending generally distally from the first locking latch 16 toward the mixer conduit 42. The first squeeze handle 70 defines a slightly arcuate profile along its length to provide a gripping surface 72 for a user's fingers to actuate movement of the first locking latch 16. It will be appreciated that the contour or profile of the first squeeze handle 70 may be modified in other embodiments, such as being modified to be generally planar. As described in further detail below, the first squeeze handle 70 is configured to be squeezed or depressed toward the mixer conduit 42 to force slight pivoting of the first locking latch 16 away from the locking notch 40. The mixer 14 and the first locking latch 16 (as well as the cartridge 12) are typically formed by injection molding a plastic material such as polypropylene or nylon, which advantageously has enough elasticity to enable slight pivoting of the first locking latch 16 at the base 60 and automatic return to the original shape after pivoting around the locking notch 40.

In operation, the mixer 14 is connected to the cartridge 12 by the following process. The inlet socket 48 of the mixer 14 is aligned with the outlet socket 28 on the cartridge 12 as shown in FIGS. 4 and 5. Advantageously, the combination of the first locking latch 16 and the radial projections 56 on the inlet socket 48 are collectively non-symmetrical around the periphery of the inlet socket 48 such that the inlet socket 48 can only be inserted into the outlet socket 28 in the intended orientation for aligning the fluid outlets 36a, 36b with the fluid inlets 54a, 54b. From the aligned position shown in FIGS. 4 and 5, the mixer 14 and the cartridge 12 are moved toward one another such that the radial projections 56 slide into the radial slots 38 and the first locking latch 16 snaps over the locking notch 40 to the engaged position shown in FIG. 6A. As previously discussed, the rounding or chamfering of the locking notch 40 at the ramp surface 40a and the leading surface 68 of the locking tab 64 assist with moving the first locking latch 16 over the locking notch 40. Because the locking tab 64 extends radially inwardly to abut the proximal wall 18 in the position shown in FIG. 5, the first locking latch 16 operates to reliably connect the mixer 14 and the cartridge 12 with a quick snap connection. As shown most clearly in FIG. 6A, the locking notch 40 is sized to fit within the space defined between the base 60 and the locking tab 64 on the first locking latch 16.

The fluid in the cartridge 12 may then be dispensed through the mixer conduit 42 and the dispensing outlet 50. In addition to properly orienting or coding the inlet socket 48 and the outlet socket 28, the engagement of the radial projections 56 in the radial slots 38 prevents relative rotation of the mixer 14 and the cartridge 12. This is beneficial for at least two reasons. First, the radial projections 56 resist any torque forces that may be applied to the mixer 14 or the cartridge 12 and may tend to tear the components apart otherwise. Second, the prevention of relative rotation between the mixer 14 and the cartridge 12 ensures that the fluid inlets 54*a*, 54*b* and the fluid outlets 36*a*, 36*b* are never rotated during installation or removal of the mixer 14, thereby avoiding any potential cross contamination that may result when relative rotation occurs. Thus, the cross contamination problems with conventional connecting mechanisms are not an issue for the dispensing assembly 10.

Figure 6A:
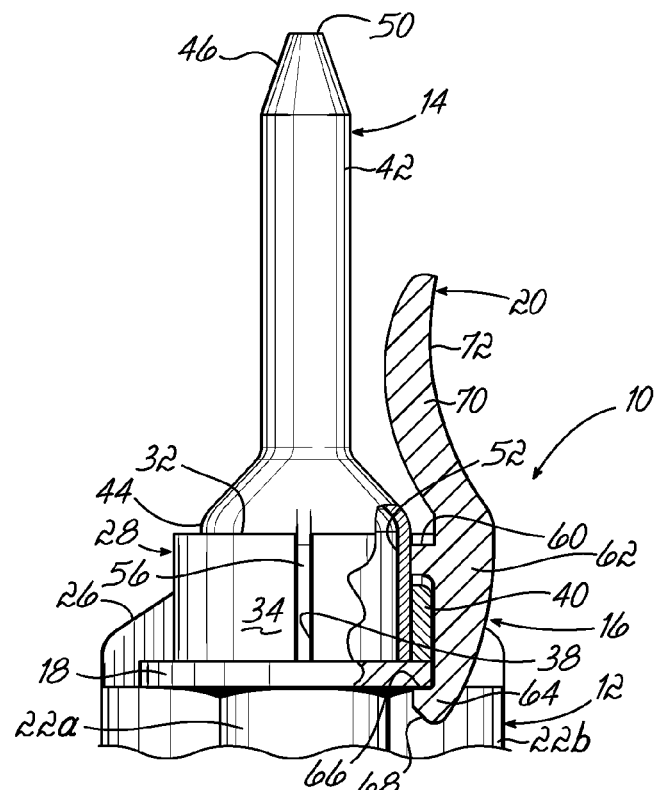
FIG. 6A is a partially cross-sectioned side view of the dispensing assembly of FIG. 1 with the first locking latch snapped into engagement with the proximal wall of the cartridge.
Figure 6B:
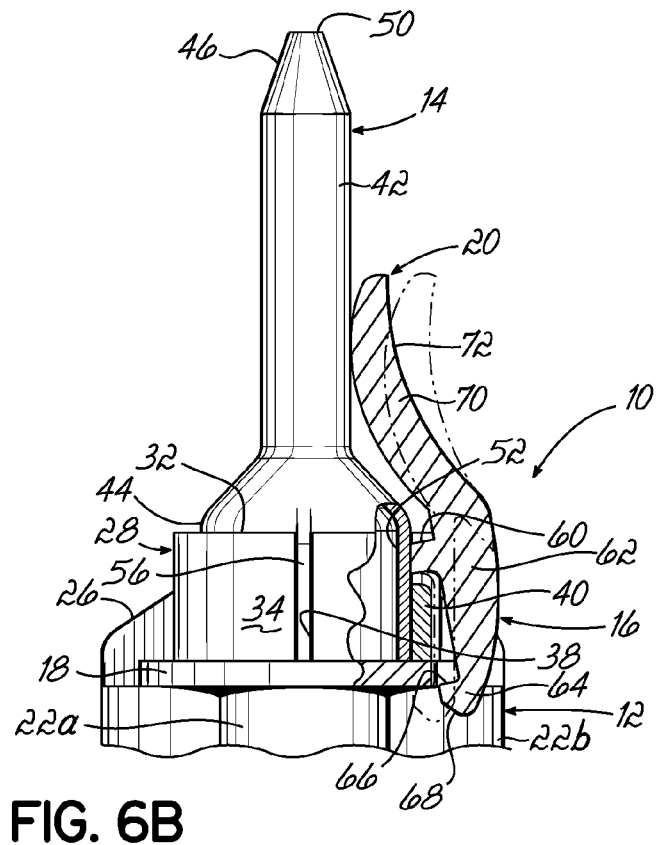
FIG. 6B is a partially cross-sectioned side view of the dispensing assembly of FIG. 6A with the first squeeze handle depressed to snap the first locking latch out of engagement with the proximal wall of the cartridge.

When the mixing and dispensing operation is completed, the mixer 14 may be removed from the cartridge 12 in a similar manner as the snap-on connection. From the position shown in FIG. 6A, a user applies manual pressure on the gripping surface 72 of the first squeeze handle 70 to pivot the first squeeze handle 70 towards the mixer conduit 42. This depression of the first squeeze handle 70 is shown in FIG. 6B and forces the arm 62 and locking tab 64 of the first locking latch 16 to pivot in an opposite direction away from engagement with the proximal wall 18 and the locking notch 40. From the position shown in FIG. 6B, the user can then freely pull the mixer 14 and the inlet socket 48 away from the outlet socket 28 and the cartridge 12, back to the disengaged position shown in FIGS. 4 and 5. As with the connection process, the disconnection of the mixer 14 from the cartridge 12 requires no relative rotation of these components and therefore reduces or eliminates the likelihood of cross contamination of fluids. Furthermore, the squeeze and snap off process for disengaging the mixer 14 from the cartridge 12 may be performed in a quick and easy manner, thereby reducing the amount of time necessary to assemble and disassemble the dispensing assembly 10. The mixer 14 and the cartridge 12 may each be formed by relatively simple injection molding processes, thereby removing any tight tolerance problems encountered with known mixer and cartridge designs. Thus, the dispensing assembly 10 of this embodiment improves upon conventional threaded or bayonet-style connection mechanisms.

With reference to FIGS. 7-10, another embodiment of a dispensing assembly 80 in accordance with the principles of the current invention is shown. In this embodiment, the dispensing assembly 80 includes a cartridge 82 that is substantially identical to the previously described cartridge 12, and therefore the same reference numbers have been applied to the same elements without further description. Additionally, the dispensing assembly 80 of this embodiment includes a mixer 84 having many of the same elements as the mixer 14 described above, and these elements have been given the same reference numbers without further description where appropriate. As with the previous embodiment, the cartridge 82 and mixer 84 are connected using a snap-on connection.

Figure 7:
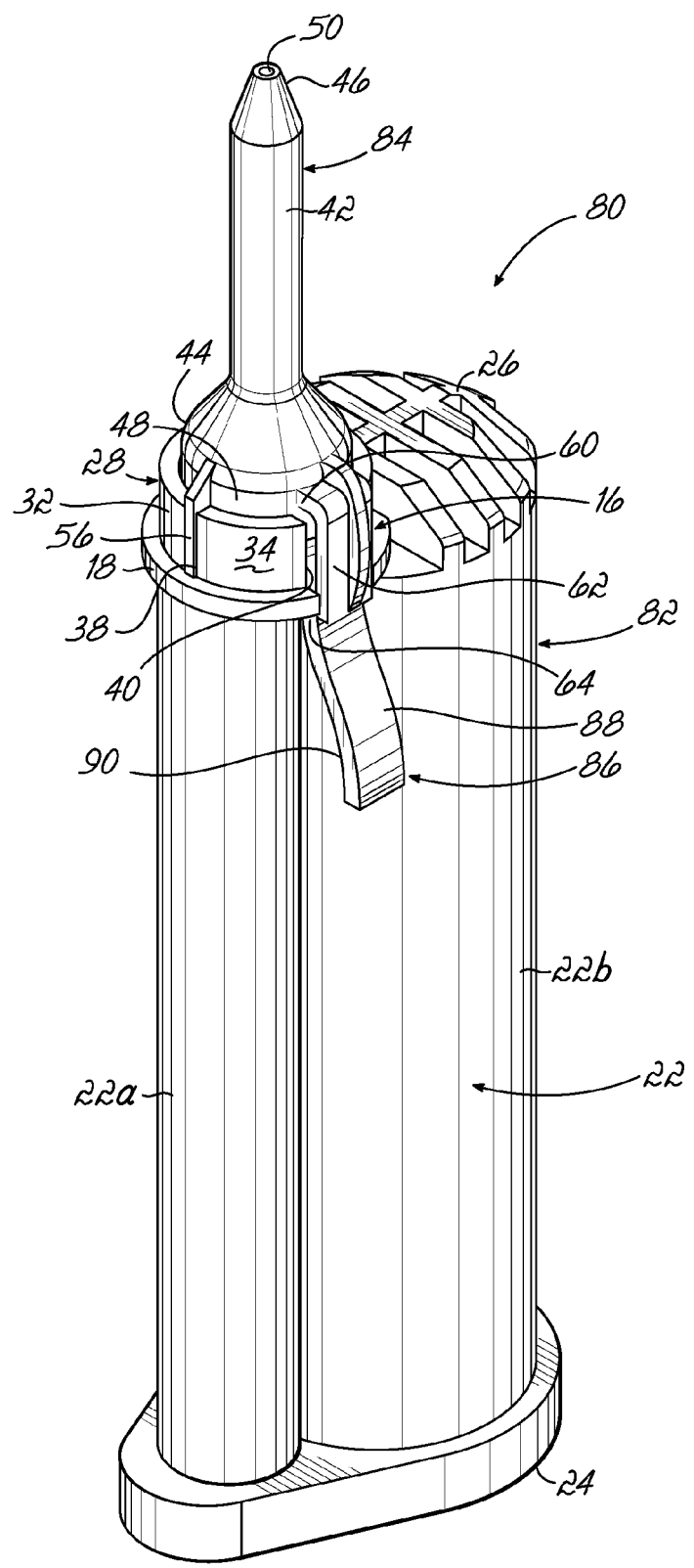
FIG. 7 is a perspective view of a dispensing assembly with a snap engagement between the mixer and the cartridge according to another embodiment of the current invention.
Figure 8:
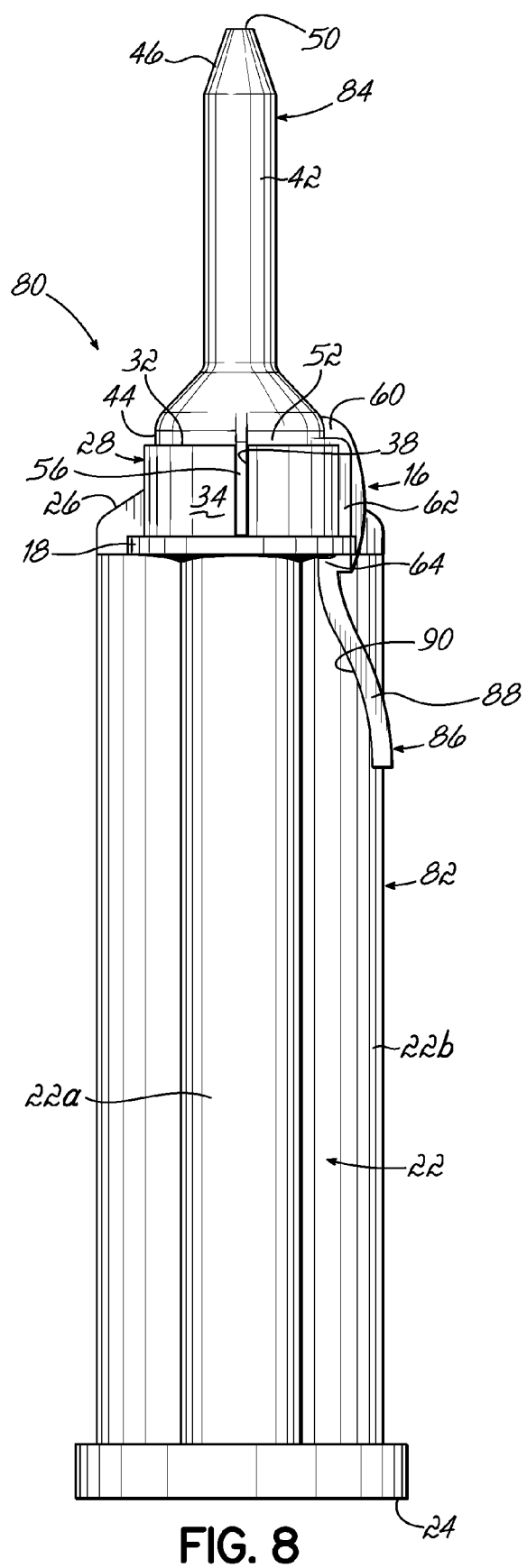
FIG. 8 is a side view of the dispensing assembly of FIG. 7 with the mixer engaged with the cartridge and showing a first locking latch on the mixer with a first peel handle extending from the first locking latch.
Figure 9:
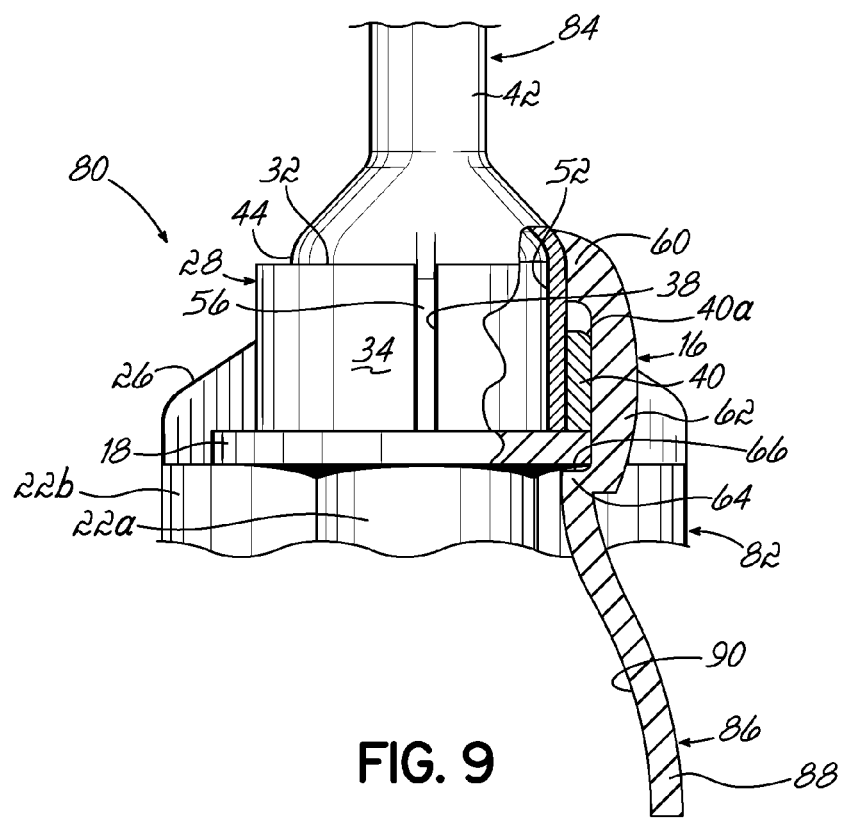
FIG. 9 is a partially cross-sectioned side view of the dispensing assembly of FIG. 7 with the first locking latch snapped into engagement with the proximal wall of the cartridge.

In this regard, the mixer 84 of this embodiment again includes a first locking latch 16 having a base 60 extending radially outwardly from an inlet socket 48, and an arm 62 extending in a proximal direction from the base 60 generally parallel to and beyond the annular wall 52 as shown in FIGS. 7 and 8. A locking tab 64 is again positioned on a free end of the arm 62 opposite the base 60 and projects radially inwardly from the arm 62. The locking tab 64 is configured to snap over a shoulder defined by the proximal wall 18 of the outlet socket 28 at the locking notch 40. Unlike the previous embodiment, the latch release mechanism 86 of this embodiment includes a first peel handle 88 connected to the first locking latch 16 adjacent the locking tab 64 and extending generally proximally from the first locking latch 16 toward the fluid chamber 22. The first peel handle 88 defines a slightly arcuate profile along its length to provide a gripping surface 90 facing toward the fluid chamber 22 for a user's fingers to actuate movement of the first locking latch 16. It will be appreciated that the contour or profile of the first peel handle 88 may be modified in other embodiments, such as being modified to be generally planar. As described in further detail below, the first peel handle 88 is configured to be pulled or peeled away from the fluid chamber 22 to force slight pivoting of the first locking latch 16 away from the locking notch 40. As with the previous embodiment, the first locking latch 16 has enough elasticity at the base 60 to enable this slight pivoting movement away from the proximal wall 18 and the locking notch 40.

In operation, the mixer 84 is connected to the cartridge 82 by the same snap-on process as described above. Accordingly, from a spaced apart position, the mixer 84 and the cartridge 82 are moved toward one another such that the radial projections 56 slide into the radial slots 38 and the first locking latch 16 snaps over the locking notch 40 to the engaged position shown in FIG. 9. The rounded or angled profile of the gripping surface 90 on the first peel handle 88 cooperates with the previously-described rounding or chamfering of the locking notch 40 at the ramp surface 40*a* in order to assist with moving the first locking latch 16 over the locking notch 40. Because the locking tab 64 extends radially inwardly to abut the proximal wall 18 in the position shown in FIG. 9, the first locking latch 16 operates to reliably connect the mixer 84 and the cartridge 82 with a quick snap connection.

Figure 10:
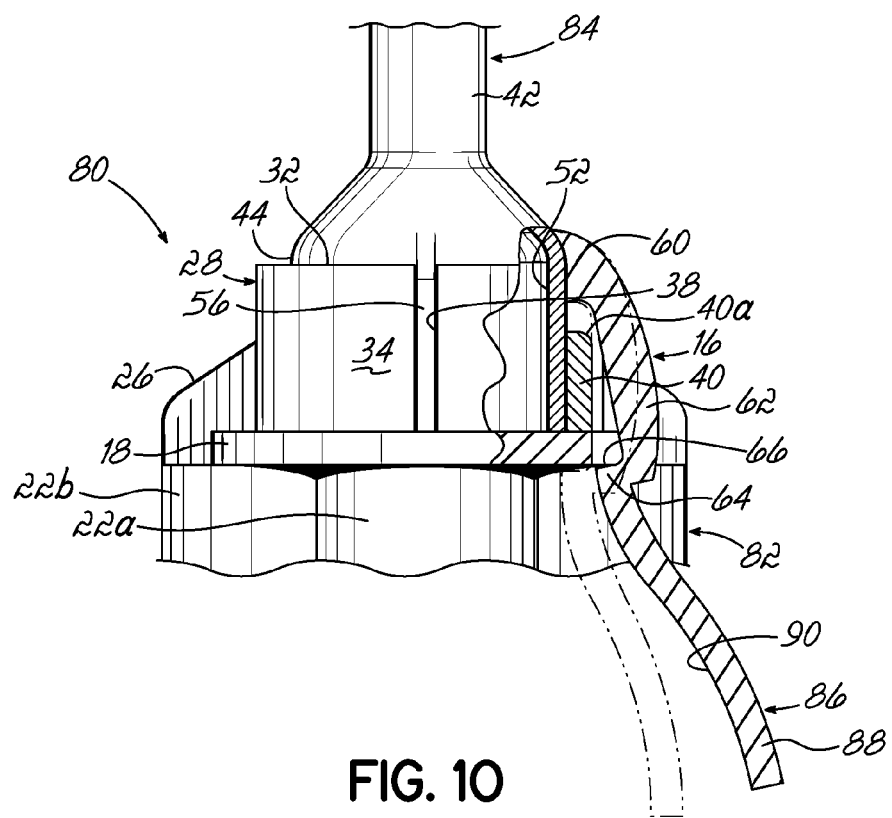
FIG. 10 is a partially cross-sectioned side view of the dispensing assembly of FIG. 9 with the first peel handle pulled away from the cartridge to snap the first locking latch out of engagement with the proximal wall of the cartridge.

The fluid in the cartridge 82 may then be dispensed through the mixer conduit 42 and the dispensing outlet 50. When the mixing and dispensing operation is completed, the mixer 84 may be removed from the cartridge 82 in a peel-off process that is substantially similar to the squeeze and snap-off process described above. More specifically, from the position shown in FIG. 9, a user applies manual pressure on the gripping surface 90 of the first peel handle 88 to pivot the first peel handle 88 away from the cartridge 82. This movement of the first peel handle 88 is shown in FIG. 10 and forces the arm 62 and locking tab 64 of the first locking latch 16 to pivot in the same direction away from engagement with the proximal wall 18 and the locking notch 40. From the position shown in FIG. 10, the user can then freely pull the mixer 84 and the inlet socket 48 away from the outlet socket 28 and the cartridge 82, back to the disengaged position. As with the connection process, the disconnection of the mixer 84 from the cartridge 82 requires no relative rotation of these components and therefore reduces or eliminates the likelihood of cross contamination of fluids. Furthermore, the peel off process for disengaging the mixer 84 from the cartridge 82 may be performed in a quick and easy manner, thereby reducing the amount of time necessary to assemble and disassemble the dispensing assembly 80.

Figure 11:
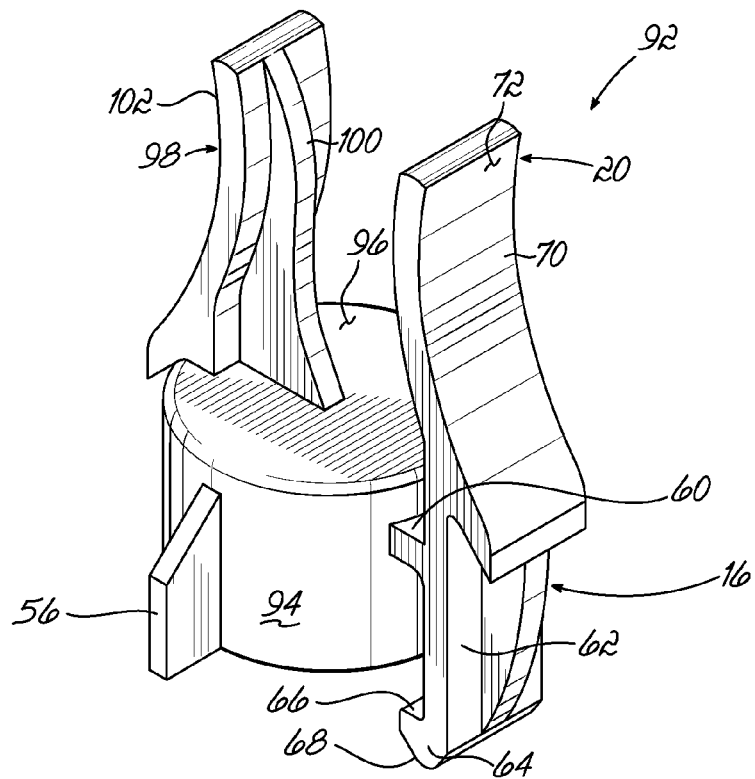
FIG. 11 is a perspective view of a sealing cap configured for use with the cartridge of FIG. 1 or 7, the sealing cap including a first locking latch and first and second squeeze handles.
Figure 12:
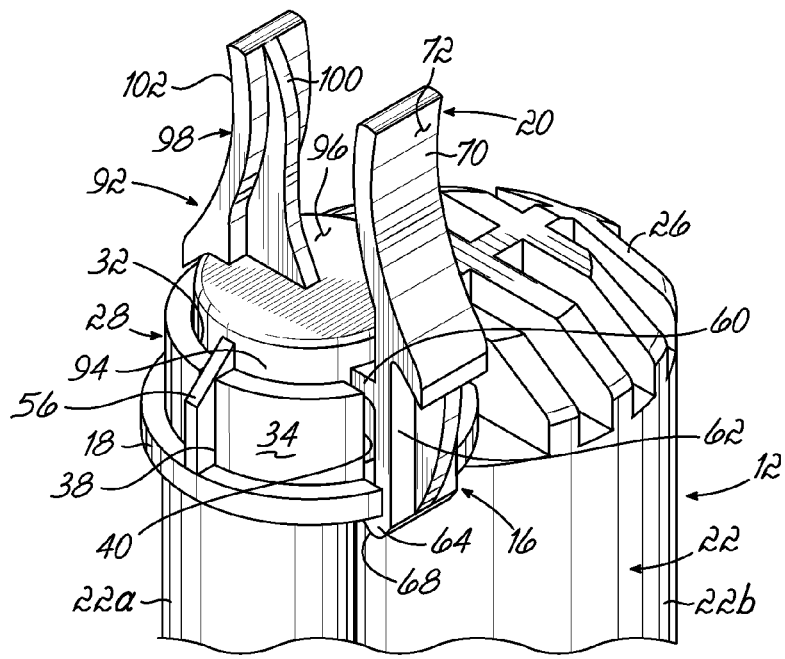
FIG. 12 is a perspective view of the sealing cap engaged with the cartridge of FIG. 1 or 7.

Before and after connection of the mixer 14, 84 to the corresponding cartridge 12, 82, a sealing cap 92 as shown in FIGS. 11 and 12 may be engaged with the outlet socket 28 to block further flow of fluid from either of the fluid outlets 36*a*, 36*b*. The sealing cap 92 includes an annular wall 94 similar to the annular wall 52 of the previously-described inlet socket 48. Furthermore, many of the same elements of the mixer 14 of the first embodiment extend from this annular wall 94 and are provided with the same reference numbers as follows: the first locking latch 16, the first squeeze handle 70, and the radial projections 56. The annular wall 94 of the sealing cap 92 terminates in a closed distal wall 96 which may include plug members (not shown) extending proximally into sealed relation with the fluid outlets 36*a*, 36*b* when the sealing cap 92 is engaged with the cartridge 12. Accordingly, the sealing cap 92 snaps onto the outlet socket 28 as shown in FIG. 12 to block further fluid flow from the fluid chamber 22 in an identical manner as the snap-on connection between the mixer 14 and the cartridge 12.

In order to enable removal of the sealing cap 92 from the cartridge 12, the sealing cap 92 also includes a second squeeze handle 98 substantially identical in contour to the first squeeze handle 70 and located on an opposite side of the annular wall 94. The second squeeze handle 98 is directly coupled to the annular wall 94 and/or the closed distal wall 96 because there is no locking latch on that side of the sealing cap 92. To this end, the second squeeze handle 98 may include a structural rib 100 connected to the closed distal wall 96 and facing toward the first squeeze handle 70. The structural rib 100 may prevent movement of the second squeeze handle 98 such that the second squeeze handle 98 can be used to provide leverage for moving the first squeeze handle 70 as described below. The second squeeze handle 98 also defines a gripping surface 102 that faces away from the first squeeze handle 70. In order to remove the sealing cap 92 from the cartridge 12, a user grips the gripping surfaces 72, 102 and squeezes the first and second squeeze handles 70, 98 toward one another to pivot the first locking latch 16 out of engagement with the proximal wall 18 and the locking notch 40 of the cartridge 12. The sealing cap 92 therefore provides a reliable and quick connection and disconnection with the cartridge 12 between installations of a mixer 14 and corresponding dispensing operations. It will be understood that further modifications to the sealing cap 92, such as the inclusion of multiple locking latches, may be made in other embodiments without departing from the scope of the invention.

Figure 13:
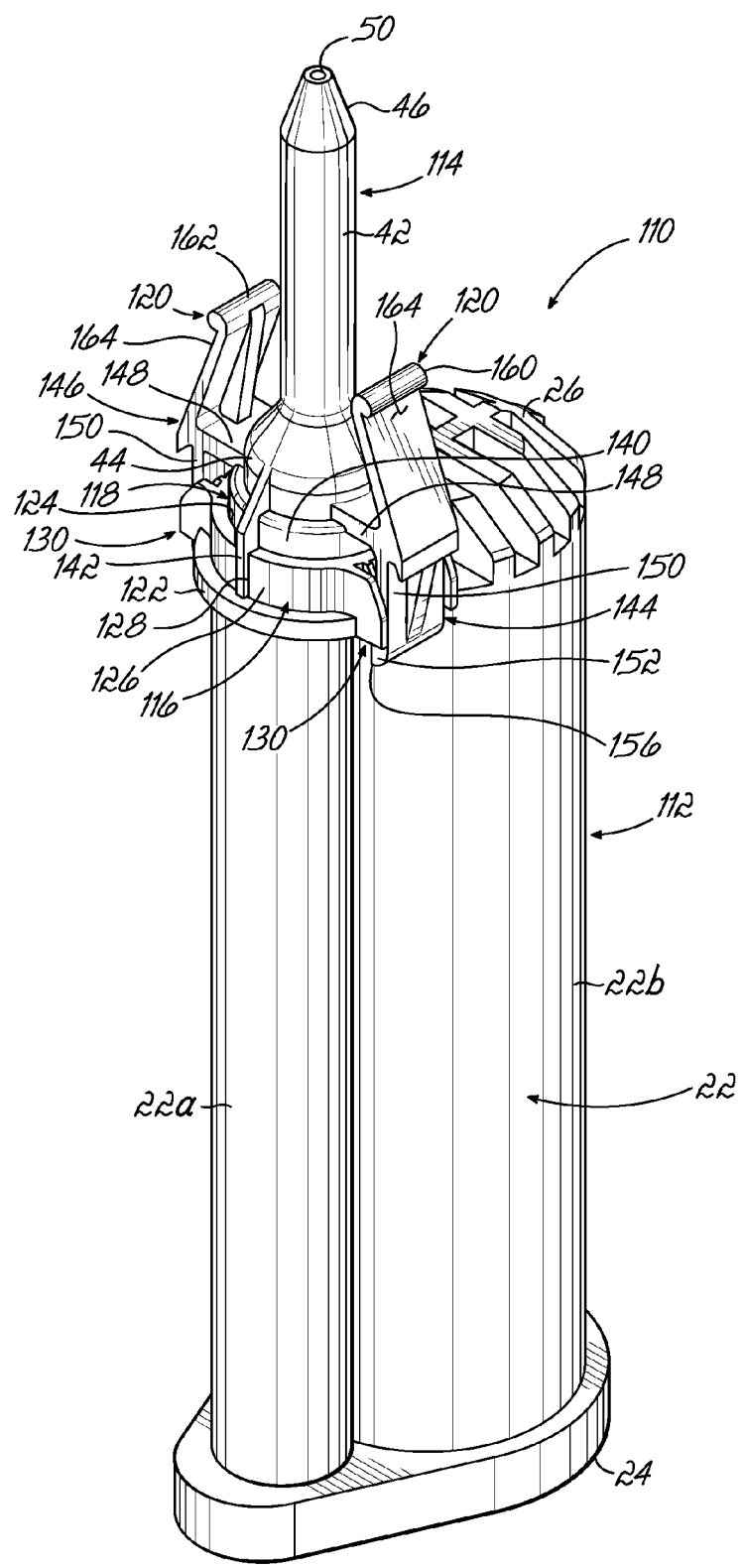
FIG. 13 is a perspective view of a dispensing assembly with a snap engagement between the mixer and the cartridge according to another embodiment of the current invention.
Figures 14, 15:
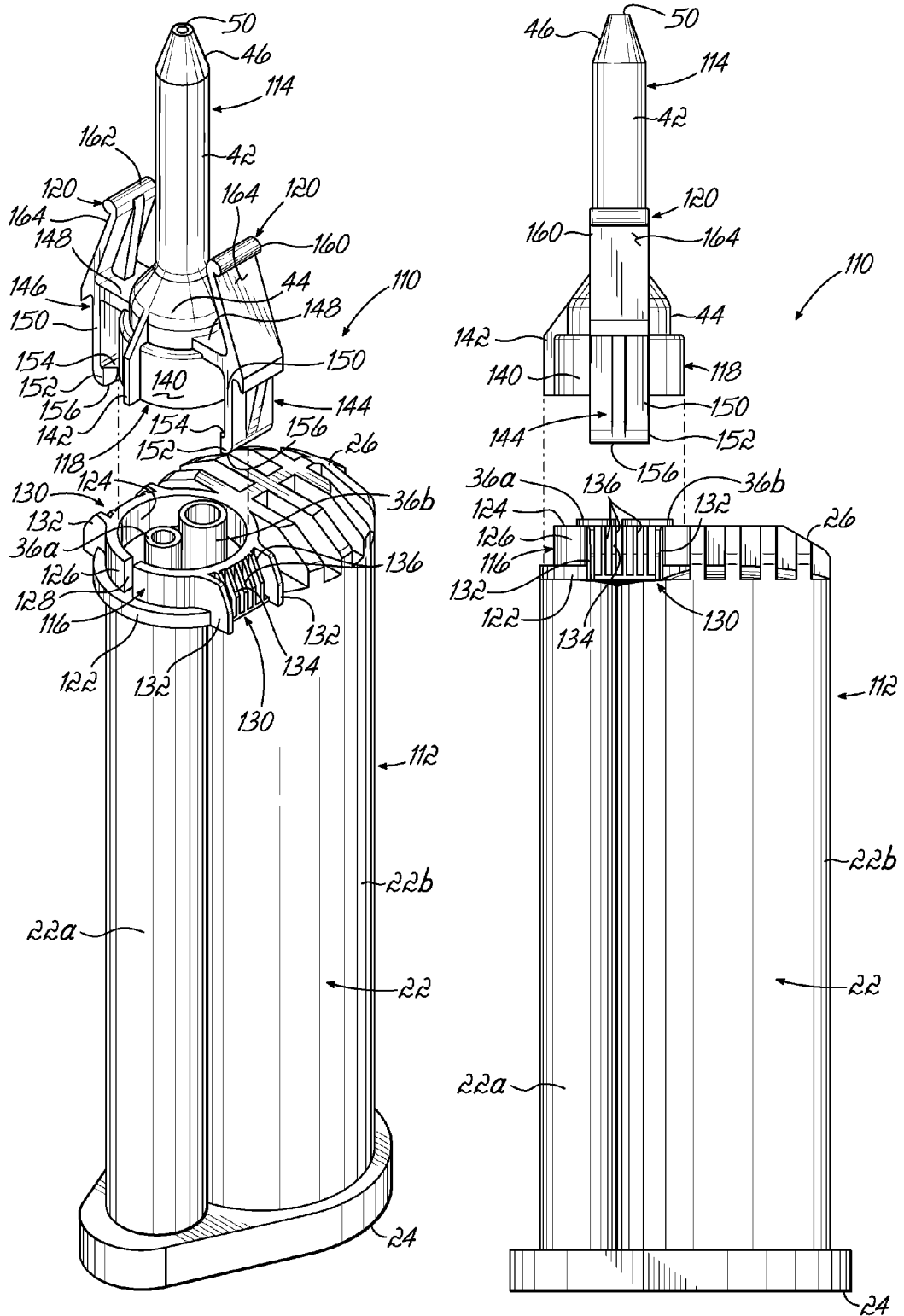
FIG. 14 is a perspective view of the dispensing assembly of FIG. 13 with the mixer disengaged from the cartridge.
FIG. 15 is a side view of the dispensing assembly of FIG. 13 showing details of first and second locking latches and first and second squeeze handles extending from the mixer.

With reference to FIGS. 13-15, another embodiment of a dispensing assembly 110 in accordance with the principles of the current invention is shown. In this embodiment, the dispensing assembly 110 includes a cartridge 112 that is similar to the previously described cartridges 12, 82 with the exception of an updated outlet socket 116, and therefore the same reference numbers have been applied to identical elements without further description (e.g., the cartridge 112 includes the same fluid chamber 22, proximal end 24, and distal end 26). Additionally, the dispensing assembly 110 of this embodiment includes a mixer 114 having an updated inlet socket 118 and many of the same elements as the mixers 14, 84 described above, and these identical elements have been given the same reference numbers without further description below (e.g., the mixer 114 includes the same mixer conduit 42 and dispensing outlet 50). As with the previous embodiment, the cartridge 112 and the mixer 114 are connected using a snap-on connection. However, the latch release mechanism 120 on the mixer 114 of this embodiment includes two opposing squeeze handles, as described in further detail below.

With particular reference to FIGS. 14 and 15, the outlet socket 116 of the cartridge 112 is shown in further detail. To this end, the outlet socket 116 of this embodiment includes a proximal wall 122 (also referred to as a proximal flange) and a hollow port 124 extending distally from the proximal wall 122. Although the hollow port 124 is shown with slightly smaller size than the proximal wall 122, it will be understood that the hollow port 124 could be resized to be the same size as the proximal wall 122 in other embodiments consistent with the invention. The hollow port 124 is formed by a generally annular wall 126 substantially surrounding the first and second fluid outlets 36a, 36b extending through the proximal wall 122 from the corresponding fluid chamber portions 22a, 22b. The first and second fluid outlets 36a, 36b are shown to be coded to different sizes, but the relative sizes of these fluid outlets 36a, 36b may be modified without departing from the scope of the invention. The generally annular wall 126 is uninterrupted about the periphery of the hollow port 32 except at a radial slot 128 formed in the annular wall 126. Additionally, a pair of locking notches 130 is formed on opposite outer-facing sides of the annular wall 126, each locking notch 130 defined by a pair of end walls 132 and a ramp surface 134 between the end walls 132. The ramp surface 134 tapers at least along a portion of the length between the distal end 26 and the proximal wall 122 for reasons set forth in further detail below. The ramp surface 134 of the illustrated embodiment includes a plurality of parallel spaced ribs 136 projecting outwardly from the annular wall 126 to reduce the total amount of material used at the ramp surface 134, although these ribs 136 could be replaced by a solid block of material in other embodiments consistent with the scope of the invention. The radial slot 128 and the locking notches 130 are configured to receive corresponding structure on the mixer 114, as described in further detail below.

As described above, the mixer 114 includes an inlet socket 118 that is located at the proximal end 44 of the mixer conduit 42, as shown in FIGS. 14 and 15. The inlet socket 118 defines a generally annular shape and is sized to be inserted into the hollow port 124 to thereby be engaged with the outlet socket 116. In this regard, the inlet socket 118 includes an annular wall 140 surrounding two fluid inlets (not shown, refer to FIG. 3 for an example). The annular wall 140 defines a slightly smaller diameter than the corresponding annular wall 126 of the outlet socket 116, although these walls 126, 140 may be resized in other embodiments of the invention. The mixer 114 also includes corresponding structure for interaction with the radial slot 128 and the locking notches 130 of the outlet socket 116. More specifically, the inlet socket 118 includes a radial projection 142 extending outwardly from the annular wall 140. The radial projection 142 is positioned and sized to slide into the radial slot 128 of the outlet socket 116 when the mixer 114 is coupled to the cartridge 112. The inlet socket 118 also includes first and second locking latches 144, 146 extending radially outwardly from opposite sides of the inlet socket 118. The first and second locking latches 144, 146 are configured to snap into engagement with the cartridge 112 by sliding over the locking notches 130.

Both of the locking latches 144, 146 are identical in construction in this embodiment, and thus only the first locking latch 144 is described in detail as follows. More particularly, the first locking latch 144 includes a base 148 projecting radially outward from the annular wall 140 and an arm 150 extending in a proximal direction from the base 148 generally parallel to and beyond the annular wall 140 as shown in FIGS. 13-15. A locking tab 152 is positioned on a free end of the arm 150 opposite the base 148 and projects radially inwardly from the arm 150. The locking tab 152 is configured to snap over a shoulder defined by the proximal wall 122 at one of the locking notches 130. Although the locking tab 152 is formed with an oblique trailing surface 154 to snugly engage or abut the proximal wall 122, the leading surface 156 of the locking tab 152 may be chamfered or rounded as shown to facilitate movement of the locking tab 152 and the arm 150 over the locking notch 130. As described above, the ramp surface 134 of the locking notch 130 is also tapered at least partially along its length to assist with this movement of the first locking latch 144 over the ramp surface 134 (e.g., the ramp surface 134 cooperates with the leading surface 156 to provide the same benefits as the ramp surface 40a in the first described embodiment). The precise appearance and contour defined by the base 148, the arm 150, and the locking tab 152 may be modified in other embodiments without departing from the scope of the current invention.

The latch release mechanism 120 of this embodiment includes a first squeeze handle 160 connected to the first locking latch 144 adjacent the base 148 and extending generally distally from the first locking latch 144 toward the mixer conduit 42. Similarly, the latch release mechanism 120 also includes a second squeeze handle 162 connected to the second locking latch 146 adjacent the base 148 and extending generally distally from the second locking latch 146 toward the mixer conduit 42. The first and second squeeze handles 160, 162 each define a generally planar profile along their lengths to provide gripping surfaces 164 for a user's fingers to actuate movement of the first and second locking latches 144, 146. It will be appreciated that the contour or profile of the first and second squeeze handles 160, 162 may be modified in other embodiments. As described in further detail below, the first and second squeeze handles 160, 162 are configured to be squeezed or depressed toward one another to force slight pivoting of the first and second locking latches 144, 146 away from the locking notches 130. As with the previous embodiments, the first and second locking latches 144, 146 are formed from a plastic material with enough elasticity at the base 148 to enable this slight pivoting movement away from the proximal wall 122 and the locking notches 130.

In operation, the mixer 114 is connected to the cartridge 112 by the same snap-on process as described above in previous embodiments. Accordingly, from a spaced apart position (FIGS. 14 and 15), the mixer 114 and the cartridge 112 are moved toward one another such that the radial projection 142 slides into the radial slot 128 and the first and second locking latches 144, 146 snap over the locking notches 130 to the engaged position shown in FIG. 13. To this end, the chamfered or rounded profile of the leading surface 156 on the locking tabs 152 cooperates with the tapered ramp surfaces 134 on the locking notches 130 in order to assist with moving the first and second locking latches 144, 146 over the proximal wall 122. Because the locking tabs 152 extend radially inwardly to abut the proximal wall 122 in the position shown in FIG. 13, the first and second locking latches 144, 146 operate to reliably connect the mixer 114 and the cartridge 112 with a quick snap connection. Advantageously, the locking features on the outlet socket 116 and the inlet socket 118 (i.e., the radial slot 128 and locking notches 130) are not completely symmetrical about the periphery of the sockets 116, 118 such that the mixer 114 may only be connected to the cartridge 112 in the desired orientation such that the fluid inlets are properly positioned relative to the fluid outlets 36a, 36b. Furthermore, the engagement of the radial projection 142 and the radial slot 128 prevents undesirable relative rotation of the mixer 114 with respect to the cartridge 112.

The fluid in the cartridge 112 may then be dispensed through the mixer conduit 42 and the dispensing outlet 50. When the mixing and dispensing operation is completed, the mixer 114 may be removed from the cartridge 112 in a squeeze and snap-off process that is substantially similar to the squeeze and snap-off process described above. More specifically, from the position shown in FIG. 13, a user applies manual pressure on the gripping surfaces 164 of the first and second squeeze handles 160, 162 to depress the first and second squeeze handles 160, 162 toward one another. This movement of the first and second squeeze handles 160, 162 forces the arms 150 and locking tabs 152 of the first and second locking latches 144, 146 to pivot in an opposite direction away from engagement with the proximal wall 122 and the locking notches 130. The user can then freely pull the mixer 114 and the inlet socket 118 away from the outlet socket 116 and the cartridge 112, back to the disengaged position in FIGS. 14 and 15. As with the connection process, the disconnection of the mixer 114 from the cartridge 112 requires no relative rotation of these components and therefore reduces or eliminates the likelihood of cross contamination of fluids. Furthermore, the squeeze and snap off process for disengaging the mixer 114 from the cartridge 112 may be performed in a quick and easy manner, thereby reducing the amount of time necessary to assemble and disassemble the dispensing assembly 110.

FIGS. 16A and 16B illustrate another embodiment of a sealing cap 170 that may be used with the outlet socket 116 of the cartridge 112 before and after connection of the mixer 114. The sealing cap 170 includes an annular wall 172 similar to the annular wall 140 of the previously-described inlet socket 118. Furthermore, many of the same or substantially similar elements of the mixer 114 described above extend from this annular wall 140 and are provided with the same reference numbers as follows: first and second locking latches 144, 146, first and second squeeze handles 160, 162 (shown with an arcuate profile in this embodiment), and the radial projection 142. The annular wall 172 of the sealing cap 170 terminates in a closed distal wall 174 which may include plug members (not shown) extending proximally into sealed relation with the fluid outlets 36a, 36b when the sealing cap 170 is engaged with the cartridge 112. Accordingly, the sealing cap 170 snaps onto the outlet socket 116 to block further fluid flow from the fluid chamber 22 in an identical manner as the snap-on connection between the mixer 114 and the cartridge 112.

The sealing cap 170 may be removed from the cartridge 112 in the same squeeze and snap off manner as previously described above for the mixer 114. In this regard, a user grips the gripping surfaces 164 and squeezes the first and second squeeze handles 160, 162 toward one another to pivot the first and second locking latches 144, 146 out of engagement with the proximal wall 122 and the locking notches 130 of the cartridge 112. The sealing cap 170 therefore provides a reliable and quick connection and disconnection with the cartridge 112 between installations of a mixer 114 and corresponding dispensing operations. In order to prevent accidental depressing of the first and second squeeze handles 160, 162 when the sealing cap 170 is initially installed on the cartridge 112, such as during shipping, the sealing cap 170 also includes a blocking member 176 positioned between and coupled to the first and second squeeze handles 160, 162 as shown in FIG. 16A. The blocking member 176 of this embodiment is a plate-shaped member molded with the first and second squeeze handles 160, 162, the blocking member 176 being configured to be broken away from the first and second squeeze handles 160, 162 (as shown in FIG. 16B) immediately before initial use of the cartridge 112 with a mixer 114. To this end, the blocking member 176 prevents accidental dislodging of the sealing cap 170 from the cartridge 112 during initial shipment and movement to the location where dispensing operations are to take place.

Yet another embodiment of a sealing cap 180 for use with the cartridge 112 of the previous embodiment is illustrated in FIGS. 17A and 17B. Similar to the previous sealing cap 170, this sealing cap 180 includes an annular wall 182, a closed distal wall 184 including plug members (not shown) surrounded by the annular wall 182, the radial projection 142, and the first and second locking latches 144, 146 extending from the annular wall 182. The sealing cap 180 also includes first and second squeeze handles 186, 188 extending distally from the first and second locking latches 144, 146. The first and second squeeze handles 186, 188 of this embodiment define L-shaped members that extend toward one another along the distal wall 184 and then bend to extend parallel to one another. As with the previous embodiment, the first and second squeeze handles 186, 188 may be depressed toward one another to pivot the first and second locking latches 144, 146 out of engagement with the proximal wall 122 and the locking notches 130 of the cartridge 112. Thus, the sealing cap 180 operates with the same snap on and squeeze and snap off operations as the previous embodiment.

Also similar to the previous embodiment, the sealing cap 180 also includes a blocking member 190 positioned between and coupled to the first and second squeeze handles 186, 188 as shown in FIG. 17A. The blocking member 190 of this embodiment is an L-shaped member molded with the first and second squeeze handles 186, 188 (and potentially also molded into engagement with the distal wall 184). The blocking member 190 is configured to be broken away from the first and second squeeze handles 186, 188 (as shown in FIG. 17B) immediately before initial use of the cartridge 112 with a mixer 114. To this end, the blocking member 190 prevents accidental dislodging of the sealing cap 190 from the cartridge 112 during initial shipment and movement to the location where dispensing operations are to take place.

With reference to FIGS. 18-20B, another embodiment of a dispensing assembly 210 in accordance with the current invention is shown. In this embodiment, the dispensing assembly 210 includes a cartridge 212 that is substantially identical to the previously described cartridge 112, and therefore the same reference numbers have been applied to the same elements without further description. Additionally, the dispensing assembly 210 of this embodiment includes a mixer 214 having several of the same elements as the mixers 14, 84, 114 described above, and these elements have been given the same reference numbers without further description where appropriate. More particularly, the mixer 214 includes a mixer conduit 42 with a proximal end 44 and a dispensing outlet 50 at a distal end 46. As with the previous embodiment, the cartridge 212 and the mixer 214 are connected using a snap-on connection.

Figure 18:
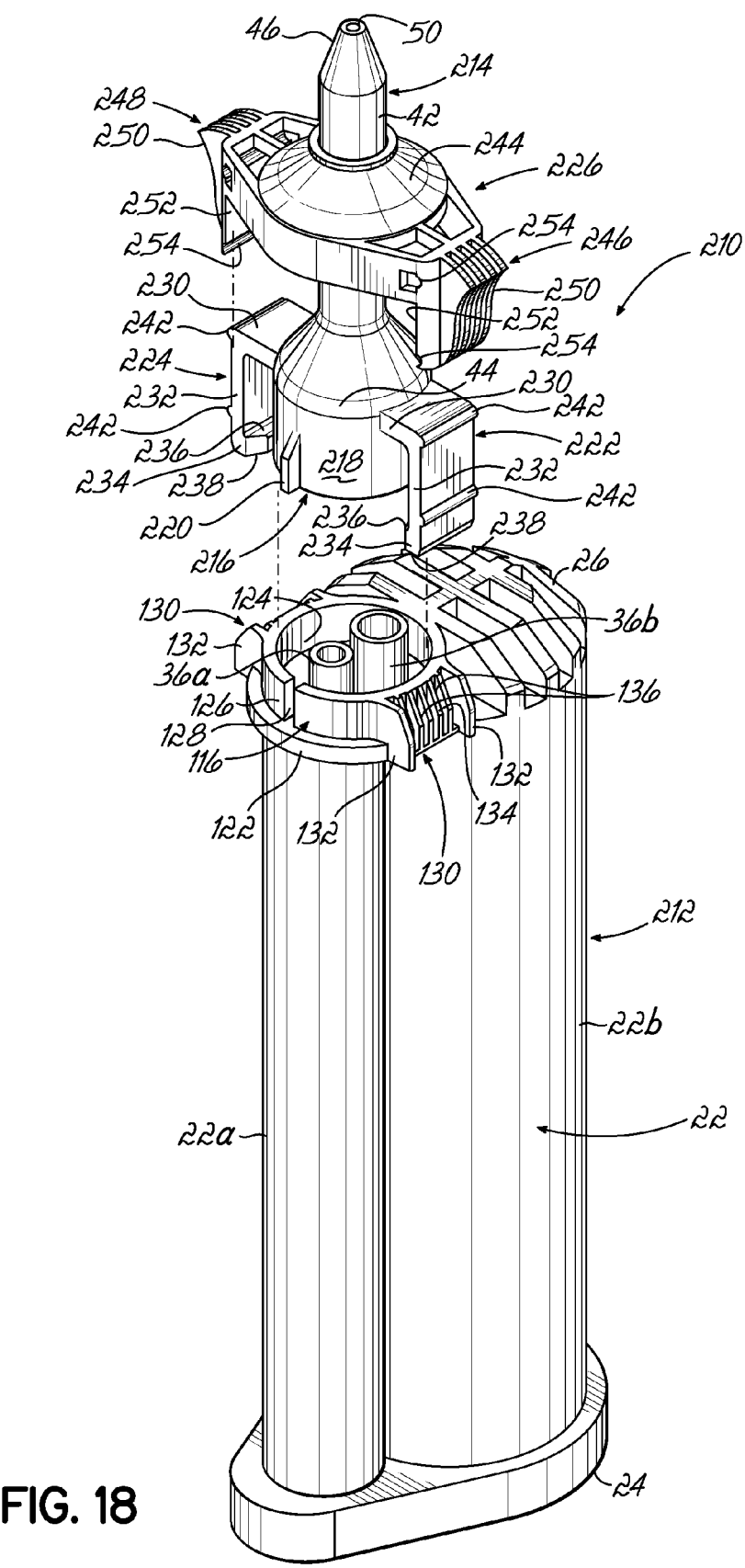
FIG. 18 is a perspective view of a dispensing assembly with a snap engagement between the mixer and the cartridge according to yet another embodiment of the current invention.
Figure 19:
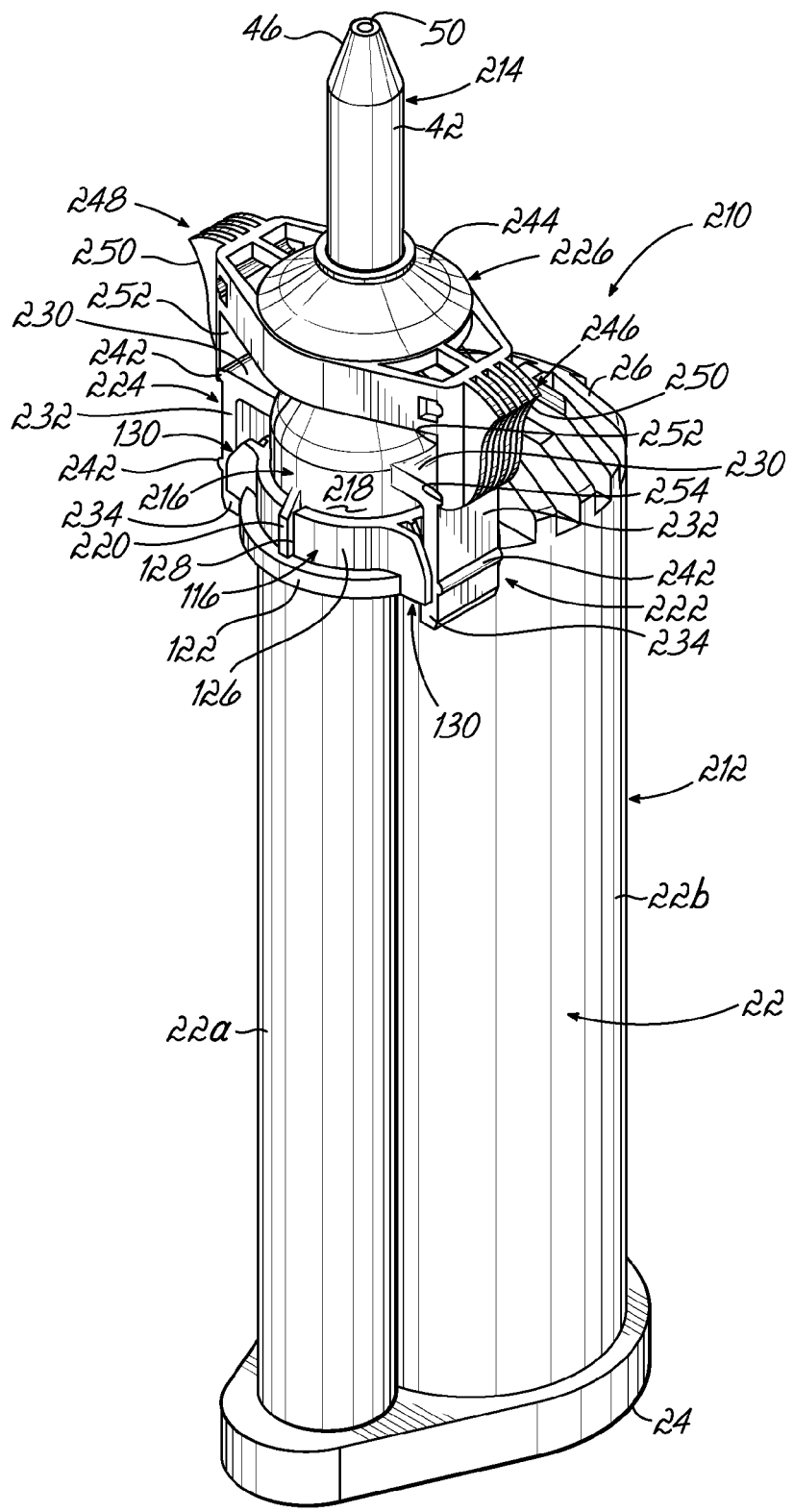
FIG. 19 is a perspective view of the dispensing assembly of FIG. 18 with the mixer engaged with the cartridge and a locking ring on the mixer in an unlocked position.

The mixer 214 of this embodiment includes an inlet socket 216 that is located at the proximal end 44 of the mixer conduit 42, as shown in FIGS. 18 and 19. The inlet socket 216 defines a generally annular shape and is sized to be inserted into the hollow port 124 to thereby be engaged with the outlet socket 116 of the cartridge 212. In this regard, the inlet socket 216 includes an annular wall 218 surrounding two fluid inlets (not shown, refer to FIG. 3 for an example). The annular wall 218 defines a slightly smaller diameter than the corresponding annular wall 126 of the outlet socket 116, although these walls 126, 218 may be resized in other embodiments of the invention. The mixer 214 also includes corresponding structure for interaction with the radial slot 128 and the locking notches 130 of the outlet socket 116. More specifically, the inlet socket 216 includes a radial projection 220 extending outwardly from the annular wall 218. The radial projection 220 is positioned and sized to slide into the radial slot 128 of the outlet socket 116 when the mixer 214 is coupled to the cartridge 212. The inlet socket 216 also includes first and second locking latches 222, 224 extending radially outwardly from opposite sides of the inlet socket 216. The first and second locking latches 222, 224 are configured to snap into engagement with the cartridge 212 by sliding over the locking notches 130 and being locked in position by a latch release mechanism 226 in the form of a locking ring 226, which is described in further detail below.

Both of the locking latches 222, 224 are identical in construction in this embodiment, and thus only the first locking latch 222 is described in detail as follows. More particularly, the first locking latch 222 includes a base 230 projecting radially outward from the annular wall 218 and an arm 232 extending in a proximal direction from the base 230 along and beyond the annular wall 218 as shown in FIGS. 18-20B. The arms 232 of the first and second locking latches 222, 224 are biased slightly outwardly from the annular wall 218 in a rest position shown most clearly in FIG. 20A. A locking tab 234 is positioned on a free end of the arm 232 opposite the base 230 and projects radially inwardly from the arm 232. The locking tab 234 is configured to snap over a shoulder defined by the proximal wall 122 at one of the locking notches 130. Although the locking tab 234 is formed with an oblique trailing surface 236 to snugly engage or abut the proximal wall 122, the leading surface 238 of the locking tab 234 may be chamfered or rounded as shown to facilitate movement of the locking tab 234 and the arm 232 over the locking notch 130. As described above, the ramp surface 134 of the locking notch 130 is also tapered at least partially along its length to assist with this movement of the first locking latch 222 over the ramp surface 134. The arm 232 also includes at least two retention projections 242 extending outwardly from the arm 232 adjacent the base 230 and proximate to the locking tab 234. These retention projections 242 are configured to interact with corresponding structure on the locking ring 226 as described below. The precise appearance and contour defined by the base 230, the arm 232, and the locking tab 234 may be modified in other embodiments without departing from the scope of the current invention.

Figure 20A:
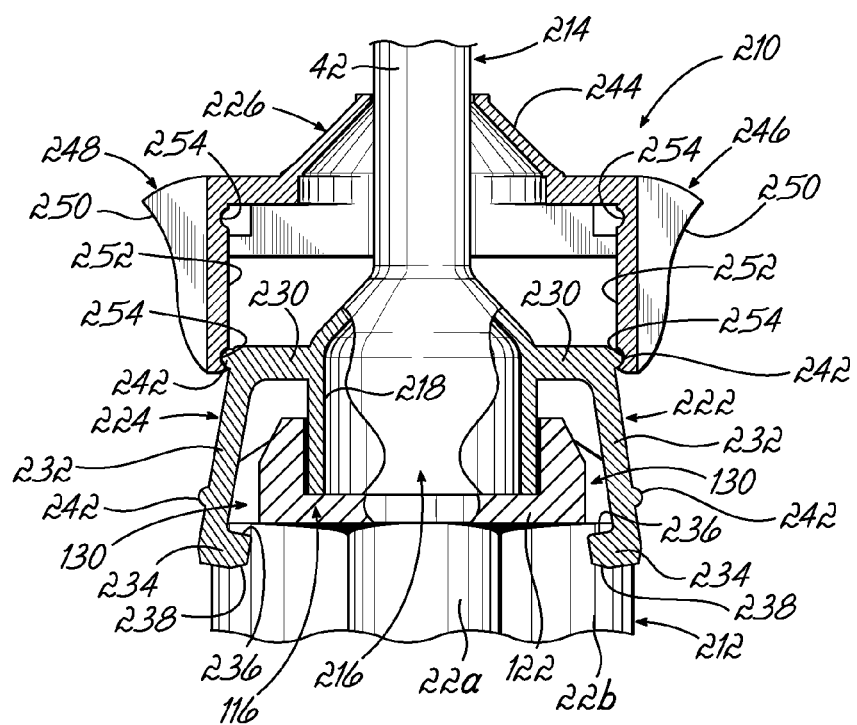
FIG. 20A is a partially cross-sectioned side view of the dispensing assembly of FIG. 19.
Figure 20B:
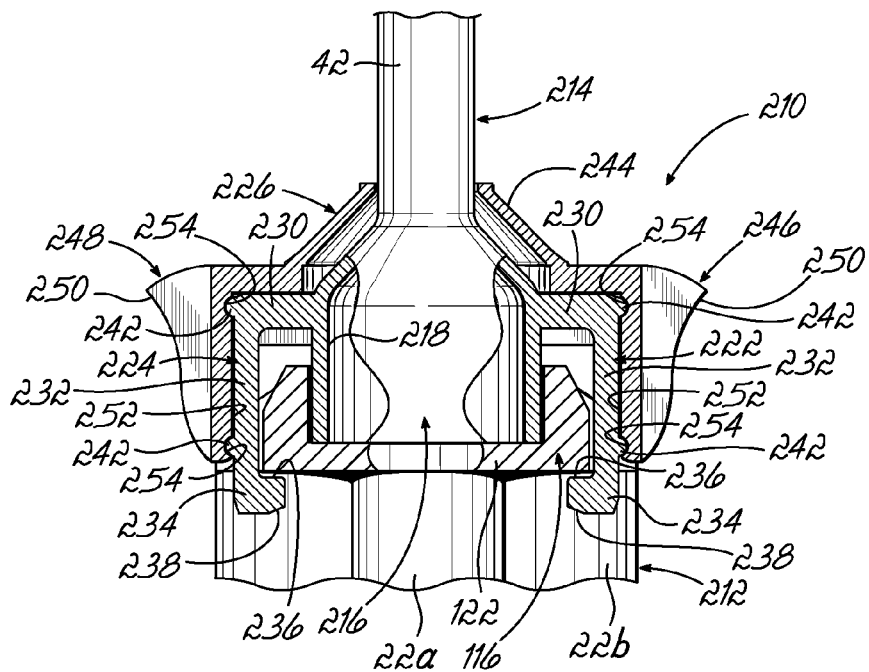
FIG. 20B is a partially cross-sectioned side view of the dispensing assembly of FIG. 19 with the locking ring on the mixer moved to a locked position.

The latch release mechanism 226 of this embodiment includes a locking ring 226 removably connected to the arms 232 of the first and second locking latches 222, 224. The locking ring 226 includes a central body 244 having a ring shape and configured to slide along the mixer conduit 42. To this end, the central body 244 defines a tapered funnel-like shape that matches the contour of the mixer conduit 42 at the intersection with the inlet socket 216. The locking ring 226 also includes two locking arms 246, 248 extending distally from opposing sides of the central body 244. Each of the locking arms 246, 248 includes an outer gripping surface 250 for manipulation by the fingers of a user and an inner surface 252 with at least two retention detents 254 configured to receive the retention projections 242 on the first and second locking latches 222, 224. The outer gripping surface 250 is defined by a plurality of spaced parallel ribs in the illustrated embodiment to save material, but this outer gripping surface 250 may be formed by a solid block of material in other embodiments consistent with the invention. The locking ring 226 is therefore configured to slide between at least two positions as shown in FIGS. 20A and 20B to force the first and second locking latches 222, 224 to snap into and out of engagement with the proximal wall 122 on the cartridge 212.

In operation, the mixer 214 is connected to the cartridge 212 by a snap-on process. Accordingly, from a spaced apart position shown in FIG. 18, the mixer 214 and the cartridge 212 are moved toward one another such that the radial projection 220 slides into the radial slot 128 and the first and second locking latches 222, 224 slide over the locking notches 130 to the engaged position shown in FIGS. 19 and 20A. The rounded or chamfered profile of the leading surface 238 of the locking tab 234 cooperates with the previously-described tapering of the ramp surface 134 in order to assist with moving the first and second locking latches 222, 224 over the locking notches 130. As shown most clearly in FIG. 20A, the locking ring 226 is located in an unlocked position in which the retention detents 254 of the locking ring 226 are only engaged with the retention projections 242 adjacent the bases 230 of the first and second locking latches 222, 224. Thus, the locking tabs 234 of the first and second locking latches 222, 224 are biased slightly outwardly from the proximal wall 122 in the rest position (e.g., the position in which the first and second locking latches 222, 224 are molded). To snap these locking tabs 234 into engagement with the proximal wall 122, a user grips the outer gripping surfaces 250 of the first and second locking arms 246, 248 and slides the locking ring 226 proximally along the first and second locking latches 222, 224 until the retention detents 254 engage the retention projections 242 proximate the locking tabs 234. The locking ring 226 is generally rigid such that the first and second locking arms 246, 248 force the first and second locking latches 222, 224 radially inwardly to the locked position shown in FIG. 20B in which the locking tabs 234 engage the proximal wall 122 of the cartridge 212. The engagement of the retention detents 254 and the retention projections 242 holds the first and second locking latches 222, 224 in this locked and snapped on position until the locking ring 226 is moved back to the unlocked position as described below.

The fluid in the cartridge 212 may then be dispensed through the mixer conduit 42 and the dispensing outlet 50. When the mixing and dispensing operation is completed, the mixer 214 may be removed from the cartridge 212 in a snap-off process. More specifically, from the position shown in FIG. 20B, a user applies manual pressure on the gripping surfaces 250 of the first and second locking arms 246, 248 to slide the locking ring 226 back to the unlocked position shown in FIG. 20A. This movement of the locking ring 226 permits the first and second locking latches 222, 224 to resiliently expand back outwardly to a rest position in which the locking tabs 234 are disengaged from the proximal wall 122. From the position shown in FIG. 20A, the user can then freely pull the mixer 214 and the inlet socket 216 away from the outlet socket 116 of the cartridge 212, back to the disengaged position. As with the connection process, the disconnection of the mixer 214 from the cartridge 212 requires no relative rotation of these components and therefore reduces or eliminates the likelihood of cross contamination of fluids. Furthermore, the movement of the locking ring 226 between locked and unlocked positions may be performed in a quick and easy manner, thereby reducing the amount of time necessary to assemble and disassemble the dispensing assembly 210.

With reference to FIGS. 21-23C, another embodiment of a dispensing assembly 310 in accordance with the current invention is shown. In this embodiment, the dispensing assembly 310 includes a cartridge 312 that is similar to the previously described cartridges 12, 82, 112, 212 with the exception of an updated outlet socket 316, and therefore the same reference numbers have been applied to identical elements without further description (e.g., the cartridge 312 includes the same fluid chamber 22, proximal end 24, and distal end 26). Although the specific appearance of the distal end 26 has been slightly modified in this embodiment compared to previous embodiments, it will be understood that this appearance may be further modified without departing from the scope of the current invention. Additionally, the dispensing assembly 310 of this embodiment includes a mixer 314 having an updated inlet socket 318 and many of the same elements as the previously-described mixer 214, and these identical elements have been given the same reference numbers without further description below (e.g., the mixer 314 includes the same mixer conduit 42 and dispensing outlet 50). The mixer 314 of this embodiment differs from the previous embodiment in that the latch release mechanism 320 includes both first and second squeeze handles 322, 324 as well as a locking ring 326. As with previous embodiments, the cartridge 312 and the mixer 314 are connected using a snap-on connection.

Figure 21:
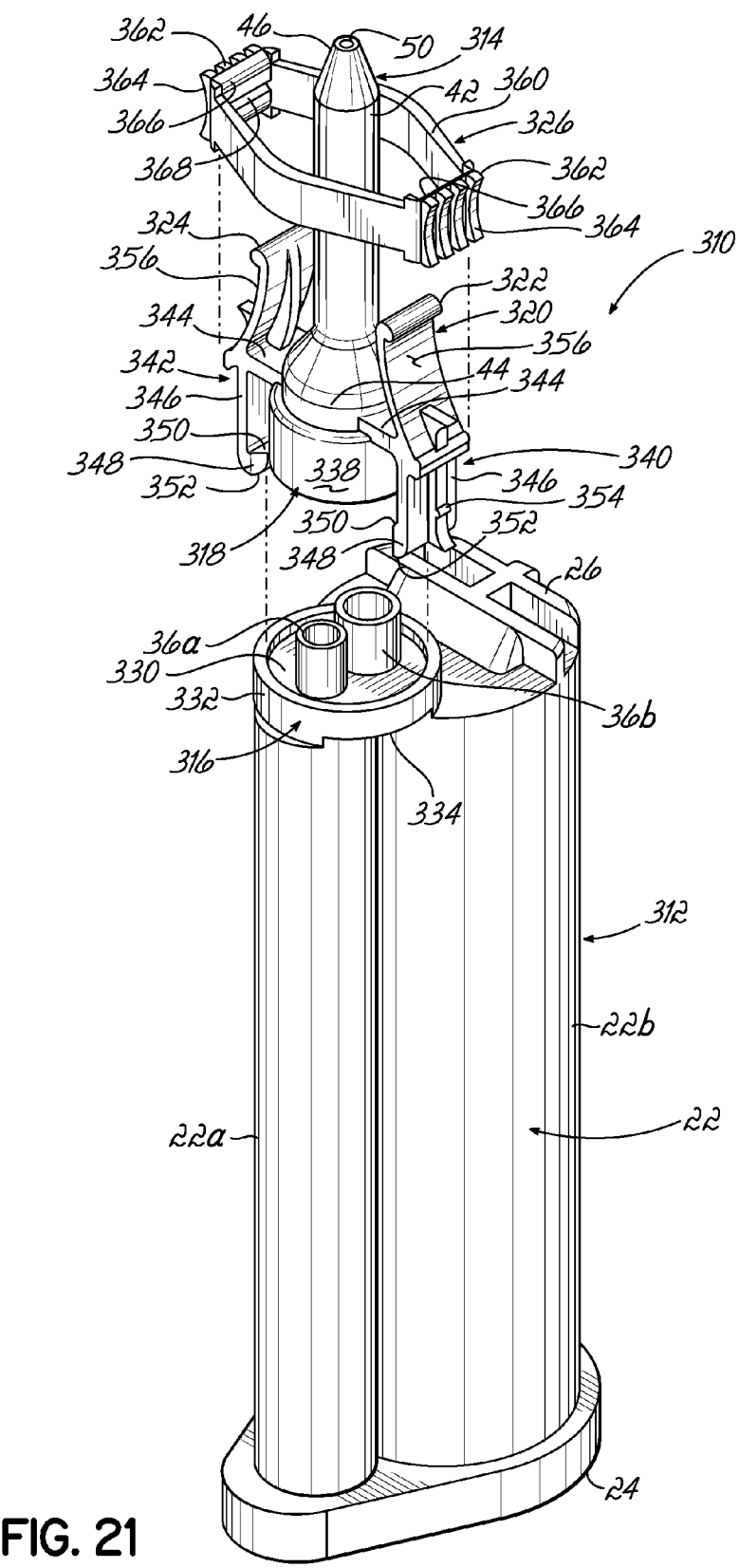
FIG. 21 is a perspective view of a dispensing assembly with a snap engagement between the mixer and the cartridge according to a further embodiment of the current invention.
Figure 22:
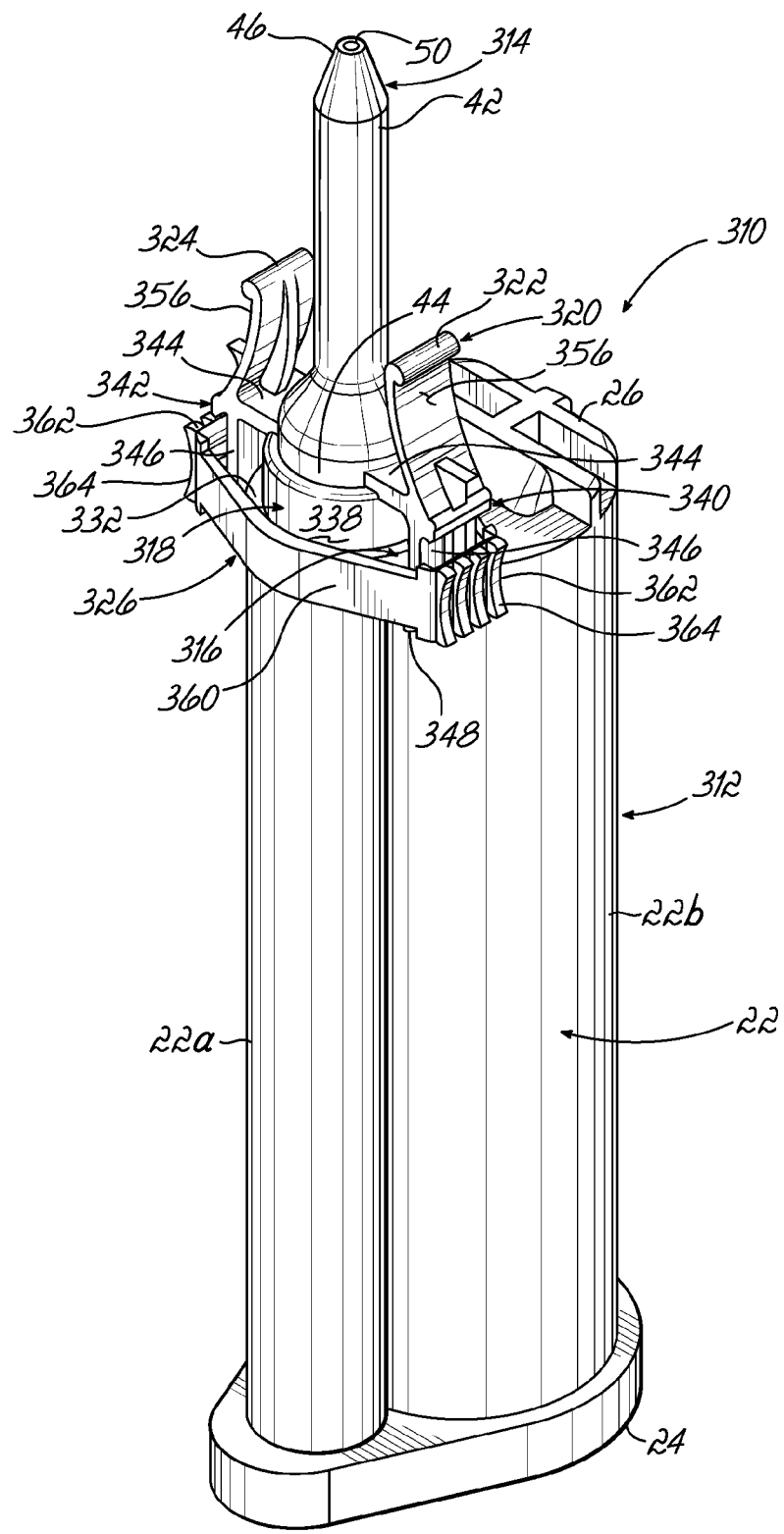
FIG. 22 is a perspective view of the dispensing assembly of FIG. 21 with the mixer engaged with the cartridge and a locking ring on the mixer in a locked position.

With particular reference to FIGS. 21 and 22, the outlet socket 316 of the cartridge 312 is shown in further detail. To this end, the outlet socket 316 of this embodiment includes a proximal wall 330 and an annular wall 332 extending distally from the proximal wall 330. In contrast to previous embodiments, the annular wall 332 defines generally the same diameter as the proximal wall 330 and does not extend distally farther than first and second fluid outlets 36a, 36b extending from the proximal wall 330. In this regard, the annular wall 332 does not substantially surround the first and second fluid outlets 36a, 36b as in other embodiments. Additionally, the annular wall 332 is uninterrupted about the periphery of the proximal wall 330. A pair of recessed locking notches 334 are formed in the proximal wall 330 on opposing sides as shown in FIG. 21 (only one of the locking notches 334 is visible). It will be understood that the locking notches 334 are offset from an axis of symmetry of the outlet socket 316 such that the snap engagement of the mixer 314 to the cartridge 312 is automatically oriented properly to code fluid inlets (not shown) of the mixer 314 to the fluid outlets 36a, 36b as described in further detail below. The locking notches 334 are configured to receive corresponding structure on the mixer 314, similar to previous embodiments.

The mixer 314 of this embodiment includes an inlet socket 318 that is located at the proximal end 44 of the mixer conduit 42, as shown in FIGS. 21 and 22. The inlet socket 318 defines a generally annular shape and is sized to be inserted at least partially into the outlet socket 316 of the cartridge 312. In this regard, the inlet socket 318 includes an annular wall 338 surrounding two fluid inlets (not shown, refer to FIG. 3 for an example). The annular wall 338 defines a slightly smaller diameter than the corresponding annular wall 332 of the outlet socket 316, although these walls 332, 338 may be resized in other embodiments of the invention. The mixer 314 also includes corresponding structure for interaction with the locking notches 334 of the proximal wall 330. More specifically, the inlet socket 318 includes first and second locking latches 340, 342 extending radially outwardly from opposite sides of the inlet socket 318. As with the locking notches 334, the first and second locking latches 340, 342 are offset slightly from an axis of symmetry of the inlet socket 318 such that the mixer 314 defines a non-symmetrical shape that only snaps onto the cartridge 312 in the desired orientation. The first and second locking latches 340, 342 are configured to snap into engagement with the cartridge 312 by sliding over the annular wall 332 into engagement with the locking notches 334 and being selectively locked in position by the latch release mechanism 320.

Both of the locking latches 340, 342 are identical in construction in this embodiment, and thus only the first locking latch 340 is described in detail as follows. More particularly, the first locking latch 340 includes a base 344 projecting radially outward from the annular wall 338 and an arm 346 extending in a proximal direction from the base 344 generally parallel to and beyond the annular wall 338 as shown in FIGS. 21-23C. A locking tab 348 is positioned on a free end of the arm 346 opposite the base 344 and projects radially inwardly from the arm 346. The locking tab 348 is configured to snap over a shoulder defined by the proximal wall 330 at one of the locking notches 334. The locking tab 348 is formed with an oblique trailing surface 350 to snugly engage or abut the proximal wall 330, and a leading surface 352 of the locking tab 348 may be chamfered or rounded as shown to facilitate movement of the locking tab 348 and the arm 346 over the annular wall 332 of the outlet socket 316. The arm 346 also includes at least two retention projections 354 extending outwardly from the arm 346 adjacent the base 344 and proximate to the locking tab 348. These retention projections 354 are configured to interact with corresponding structure on the locking ring 326 as described below. The precise appearance and contour defined by the base 344, the arm 346, and the locking tab 348 may be modified in other embodiments without departing from the scope of the current invention.

The latch release mechanism 320 of this embodiment includes the first and second squeeze handles 322, 324, which are connected to the corresponding first and second locking latches 340, 342 adjacent the bases 344 and extending generally distally from the first and second locking latches 340, 342 toward the mixer conduit 42. The first and second squeeze handles 322, 324 each define a generally arcuate profile along their lengths to provide gripping surfaces 356 for a user's fingers to actuate movement of the first and second locking latches 340, 342. It will be appreciated that the contour or profile of the first and second squeeze handles 322, 324 may be modified in other embodiments. As described in further detail below, the first and second squeeze handles 322, 324 are configured to be squeezed or depressed toward one another to force slight pivoting of the first and second locking latches 340, 342 away from the locking notches 334. As with the previous embodiments, the first and second locking latches 340, 342 are formed from a plastic material with enough elasticity at the base 344 to enable this slight pivoting movement away from the proximal wall 330 and the locking notches 334.

Figure 23A:
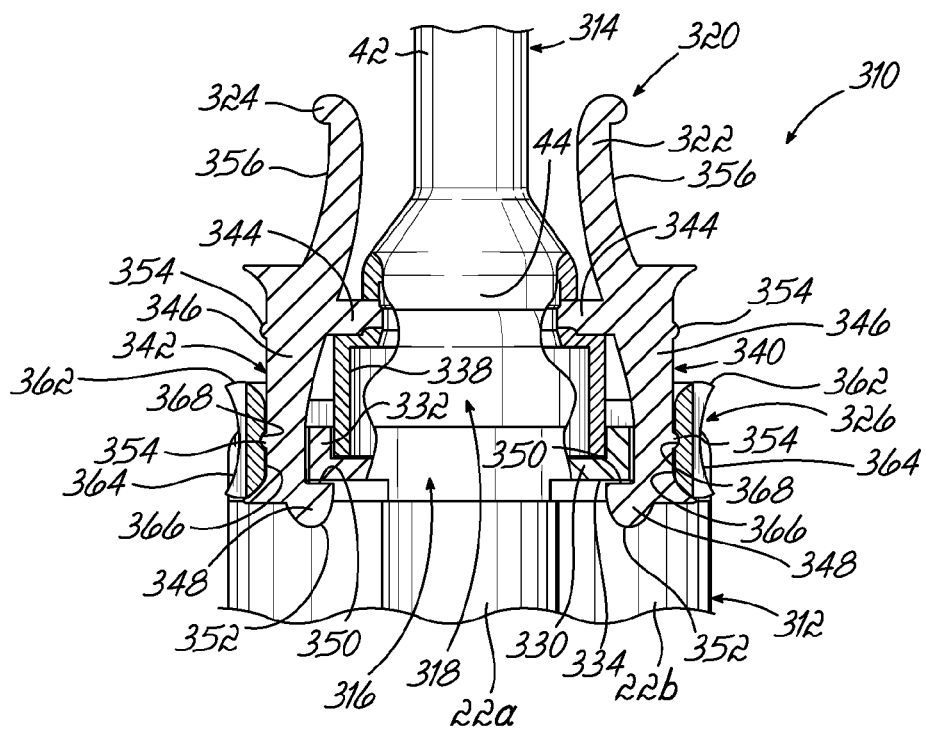
FIG. 23A is a partially cross-sectioned side view of the dispensing assembly of FIG. 21 with the locking ring in a locked position on first and second locking latches.
Figure 23B:
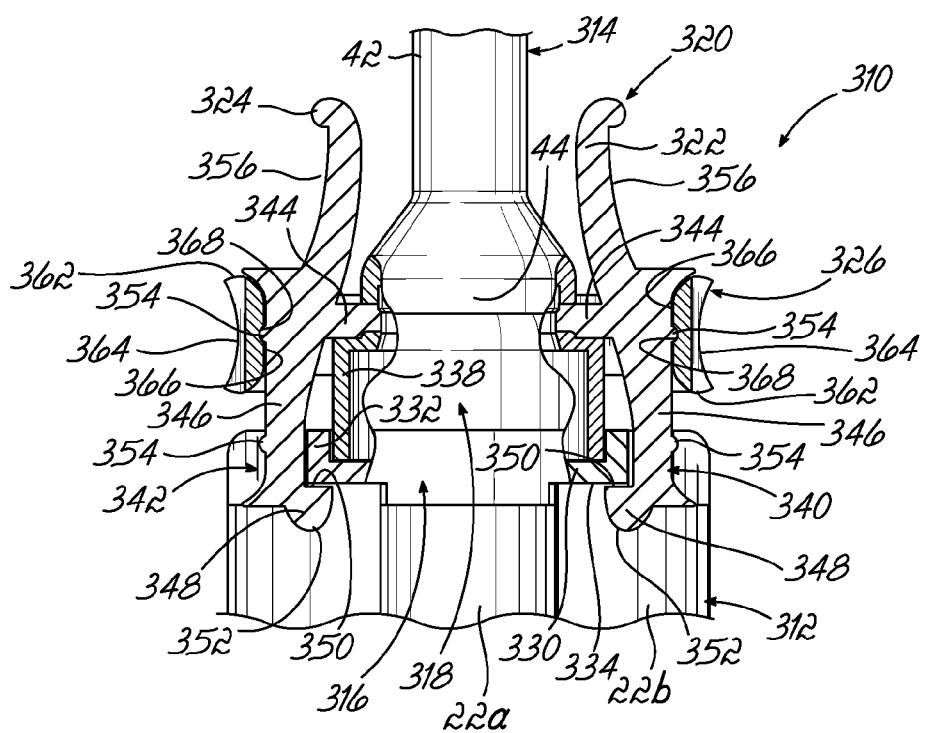
FIG. 23B is a partially cross-sectioned side view of the dispensing assembly of FIG. 23A with the locking ring in an unlocked position on the first and second locking latches.

The latch release mechanism 320 of this embodiment also includes a locking ring 326 connected to the arms 346 of the first and second locking latches 340, 342. The locking ring 326 includes a central body 360 having a ring shape configured to wrap around the inlet socket 318 and the first and second locking latches 340, 342. The locking ring 326 also includes first and second locking members 362 on opposite sides of the central body 360 and located adjacent the arms 346 of the first and second locking latches 340, 342. The locking members 362 are identical and each includes an outer gripping surface 364 for manipulation by the fingers of a user and an inner surface 366 with a retention detent 368 configured to receive one of the retention projections 354 on the first and second locking latches 340, 342. The outer gripping surface 364 is defined by a plurality of spaced parallel ribs in the illustrated embodiment to save material, but this outer gripping surface 364 may be formed by a solid block of material in other embodiments consistent with the invention. The locking ring 326 is therefore configured to slide between at least two positions as shown in FIGS. 23A and 23B to selectively enable or prevent the actuation of the first and second squeeze handles 322, 324 to snap the first and second locking latches 340, 342 out of engagement with the proximal wall 330 on the cartridge 312.

In operation, the mixer 314 is connected to the cartridge 312 by a snap-on process. Accordingly, from a spaced apart position shown in FIG. 21, the mixer 314 and the cartridge 312 are moved toward one another such that the first and second locking latches 340, 342 slide over the annular wall 332 adjacent the locking notches 334 to the engaged position shown in FIG. 23B. As shown most clearly in FIG. 23B, the locking ring 326 is located in an unlocked position in which the retention detents 368 of the locking ring 326 are engaged with the retention projections 354 adjacent the bases 344 of the first and second locking latches 340, 342, thereby enabling pivoting movement of the locking tabs 348 over the annular wall 332. To lock the first and second locking latches 340, 342 in the engaged position, a user grips the outer gripping surfaces 364 of the locking members 362 and moves the locking ring 326 proximally so that the retention detents 368 engage the retention projections 354 proximate to the locking tabs 348. In this locked position of the locking ring 326 shown in FIG. 23A, the locking ring 326 prevents pivotal movement of the arms 346 and the locking tabs 348 away from the proximal wall 330. The engagement of the retention detents 368 and the retention projections 354 thereby holds the first and second locking latches 340, 342 in this locked and snapped on position until the locking ring 326 is moved back to the unlocked position as described below.

Figure 23C:
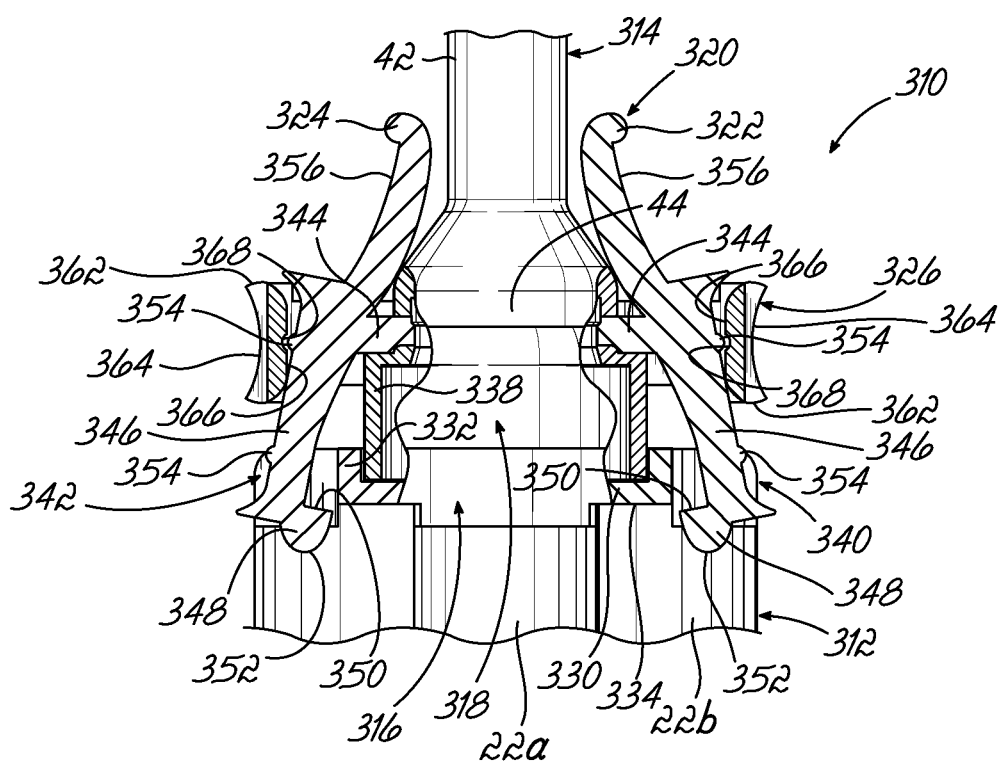
FIG. 23C is a partially cross-sectioned side view of the dispensing assembly of FIG. 23A with the locking ring in the unlocked position and first and second squeeze handles depressed to snap the first and second locking latches out of engagement with a proximal wall of the cartridge.

The fluid in the cartridge 312 may then be dispensed through the mixer conduit 42 and the dispensing outlet 50. When the mixing and dispensing operation is completed, the mixer 314 may be removed from the cartridge 312 in an unlocking and snap-off process. More specifically, from the position shown in FIG. 23A, a user applies manual pressure on the gripping surfaces 364 of the locking members 362 to slide the locking ring 326 distally back to the unlocked position shown in FIG. 23B. This movement of the locking ring 326 permits the first and second locking latches 340, 342 to be actuated by depression of the first and second squeeze handles 322, 324. In this regard, a user applies force to the gripping surfaces 356 of the first and second squeeze handles 322, 324 to move these squeeze handles 322, 324 toward one another as shown in FIG. 23C, which causes the locking tabs 348 to pivot away from engagement with the proximal wall 330. From the position shown in FIG. 23C, the user can then pull the mixer 314 distally out of the snap engagement with the cartridge 312 back to the disengaged position. As with the connection process, the disconnection of the mixer 314 from the cartridge 312 requires no relative rotation of these components and therefore reduces or eliminates the likelihood of cross contamination of fluids. Furthermore, the movement of the locking ring 326 between locked and unlocked positions and the movement of the first and second squeeze handles 322, 324 may be collectively performed in a quick and easy manner, thereby reducing the amount of time necessary to assemble and disassemble the dispensing assembly 310.

With reference to FIGS. 24-26B, another embodiment of a dispensing assembly 410 in accordance with the current invention is shown. In this embodiment, the dispensing assembly 410 includes a cartridge 412 that is similar to the previously described cartridges 12, 82, 112, 212, 312 with the exception of an updated outlet socket 416, and therefore the same reference numbers have been applied to identical elements without further description (e.g., the cartridge 412 includes the same fluid chamber 22, proximal end 24, and distal end 26). Additionally, the dispensing assembly 410 of this embodiment includes a mixer 414 having an updated inlet socket 418 and many of the same elements as the previously-described mixer 314, and these identical elements have been given the same reference numbers without further description below (e.g., the mixer 414 includes the same mixer conduit 42 and dispensing outlet 50). The mixer 414 of this embodiment differs from the previous embodiment in that the inlet socket 418 includes a plurality of locking latches 420 configured to substantially surround the outlet socket 416, and a latch release mechanism 422 includes only a locking ring 424. As with previous embodiments, the cartridge 412 and the mixer 414 are connected using a snap-on connection.

Figure 24:
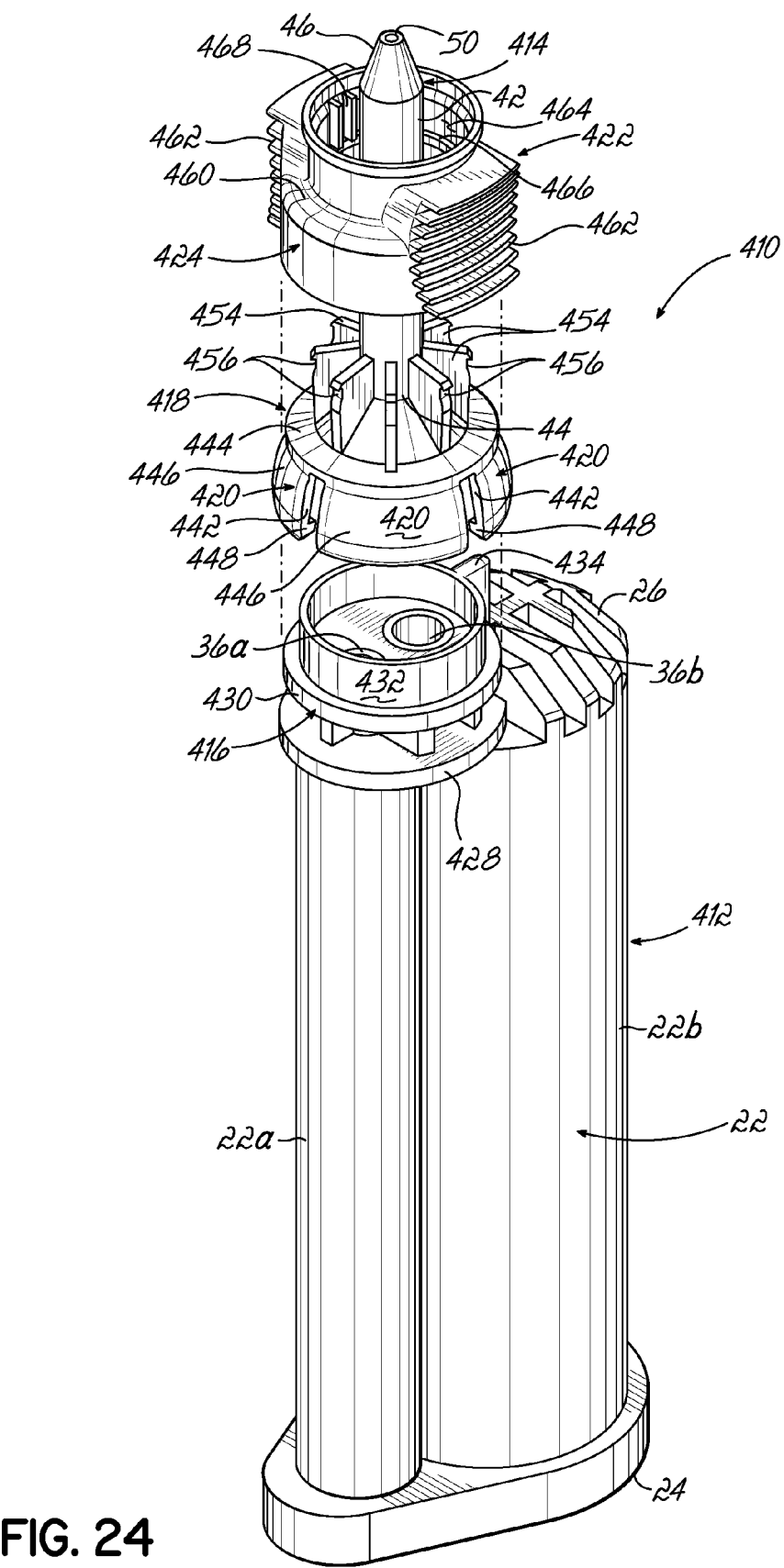
FIG. 24 is a perspective view of a dispensing assembly with a snap engagement between the mixer and the cartridge according to another embodiment of the current invention.
Figure 25:
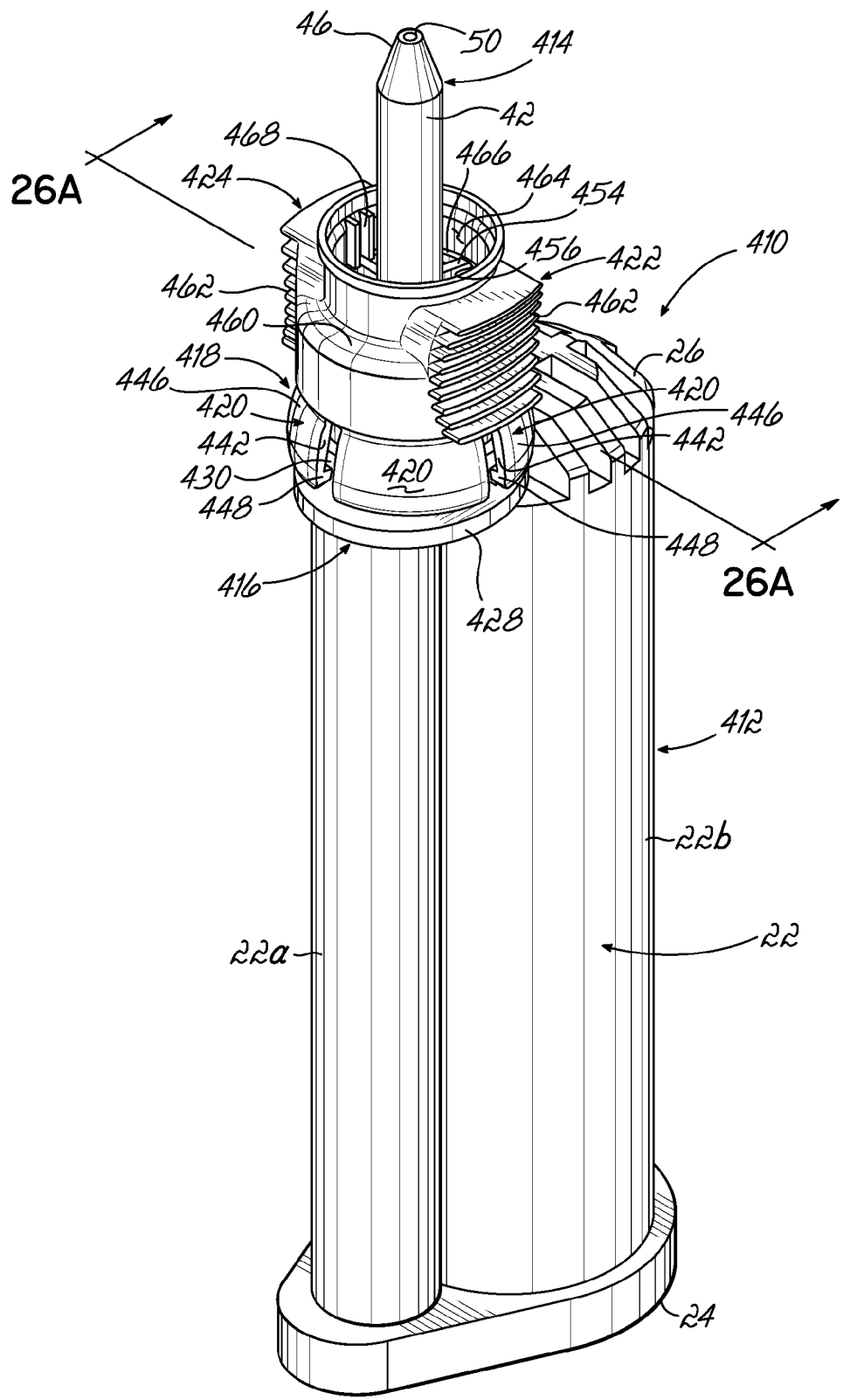
FIG. 25 is a perspective view of the dispensing assembly of FIG. 24 with the mixer engaged with the cartridge and a locking ring in an unlocked positioned on the mixer.

With particular reference to FIGS. 24 and 25, the outlet socket 416 of the cartridge 412 is shown in further detail. To this end, the outlet socket 416 of this embodiment includes a first proximal wall 428 and a second proximal wall 430 (also referred to as proximal flange) spaced distally from the first proximal wall 428. The first and second fluid outlets 36a, 36b of the cartridge 412 extend between these first and second proximal walls 428, 430 and terminate at the second proximal wall 430. The outlet socket 416 also includes a generally uninterrupted annular wall 432 extending distally from the second proximal wall 430. The annular wall 432 includes a radial projection 434 extending outwardly as shown in FIG.

24. The radial projection 434 is configured to engage corresponding structure on the inlet socket 418, similar to previous embodiments.

The mixer 414 of this embodiment includes an inlet socket 418 that is located at the proximal end 44 of the mixer conduit 42, as shown in FIGS. 24 and 25. The inlet socket 418 defines a generally annular shape and is sized to be inserted at least partially into the outlet socket 416 of the cartridge 412. In this regard, the inlet socket 418 includes an annular wall 438, a proximal end wall 440 configured to abut the second proximal wall 430 of the outlet socket 416 (see FIG. 26A), and two fluid inlets (not shown, refer to FIG. 3 for an example) extending proximally from this proximal end wall 440. The annular wall 438 defines a slightly smaller diameter than the corresponding annular wall 432 of the outlet socket 416. The mixer 414 also includes corresponding structure for interaction with the second proximal wall 430. More specifically, the inlet socket 418 includes the plurality of locking latches 420, which extend radially outwardly from the annular wall 438 of the inlet socket 418. The plurality of locking latches 420 substantially surround the inlet socket 418 but are separated from one another by radial slots 442. One of these radial slots 442 may be sized differently than the other radial slots 442 and large enough to receive the radial projection 434 of the outlet socket 416, thereby ensuring that the mixer 414 and the cartridge 412 are automatically aligned properly when the inlet socket 418 is engaged with the outlet socket 416. The plurality of locking latches 420 is configured to snap into engagement with the cartridge 412 by sliding over the annular wall 432 into engagement with the second proximal wall 430.

Each of the locking latches 420 is identical in construction in this embodiment. More particularly, each locking latch 420 includes a base 444 projecting radially outward from the annular wall 438 and an arm 446 extending in a proximal direction from the base 444 along and beyond the annular wall 438 as shown in FIGS. 24-26B. A locking tab 448 is positioned on a free end of the arm 446 opposite the base 444 and projects radially inwardly from the arm 446. The locking tab 448 is configured to snap over a shoulder defined by the second proximal wall 430. The locking tab 448 is formed with an oblique trailing surface 450 to snugly engage or abut the second proximal wall 430, and a leading surface 452 of the locking tab 448 may be chamfered or rounded as shown to facilitate movement of the locking tab 448 and the arm 446 over the annular wall 432 and over the second proximal wall 430 of the outlet socket 416. Each of the plurality of locking latches 420 is molded or otherwise formed in a rest position in which the locking latches 420 are splayed slightly outwardly from the inlet socket 418 as shown most clearly in FIG. 26A. The precise appearance and contour defined by the base 444, the arm 446, and the locking tab 448 may be modified in other embodiments without departing from the scope of the current invention.

The inlet socket 418 also includes a plurality of radial projections 454 extending outwardly from the mixer conduit 42 and positioned distally of the plurality of locking latches 420. Each of these radial projections 454 includes a locking detent 456 spaced from the plurality of locking latches 420. For example, the locking detents 456 may be located at free distal ends of the radial projections 454 as shown in FIG. 24. The locking detents 456 are configured to engage corresponding structure on the locking ring 424 as described in further detail below.

The latch release mechanism 422 of this embodiment includes the locking ring 424, which is removably connected to the mixer 414. The locking ring 424 includes a ring-shaped body 460 configured to wrap around the mixer 414 at the inlet socket 418. The locking ring 424 also includes first and second outer gripping surfaces 462 (also referred to as an exterior handle) located on opposite sides of the body 460. An inner surface 464 of the locking ring 424 includes an annular locking projection 466 configured to engage the locking detents 456 and at least one radial slot 468 configured to snugly receive one of the radial projections 454 on the inlet socket 418. In this regard, the locking ring 424 may be re-oriented to any orientation by engaging the radial slot 468 with a different radial projection 454, thereby enabling different orientations of the outer gripping surfaces 462 to a desired location. The locking ring 424 is configured to slide into and out of a locked position to selectively force the plurality of locking latches 420 into engagement with the second proximal wall 430 of the outlet socket 416.

In operation, the mixer 414 is connected to the cartridge 412 by a snap-on process. Accordingly, from a spaced apart position shown in FIG. 24, the mixer 414 and the cartridge 412 are moved toward one another such that the radial projection 434 on the outlet socket 416 slides into the largest radial slot 442 defined between the plurality of locking latches 420. The plurality of locking latches 420 slides over the annular wall 432 and the second proximal wall 430 of the outlet socket 416 to the engaged position shown in FIGS. 25 and 26A. As shown most clearly in FIG. 26A, the locking ring 424 is located in an unlocked position in which the locking ring 424 does not surround the locking latches 420 such that the locking tabs 448 of the plurality of locking latches 420 are biased slightly outwardly from the second proximal wall 430 in the rest position (e.g., the position in which the plurality of locking latches 420 are molded). To snap these locking tabs 448 into engagement with the second proximal wall 430, a user grips the outer gripping surfaces 462 of the locking ring 424 and slides the locking ring 424 proximally along the plurality of locking latches 420 until the inner surface 464 forces the plurality of locking latches 420 radially inwardly to the locked position shown in FIG. 26B in which the locking tabs 448 engage the second proximal wall 430 of the cartridge 412.

Figure 26A:
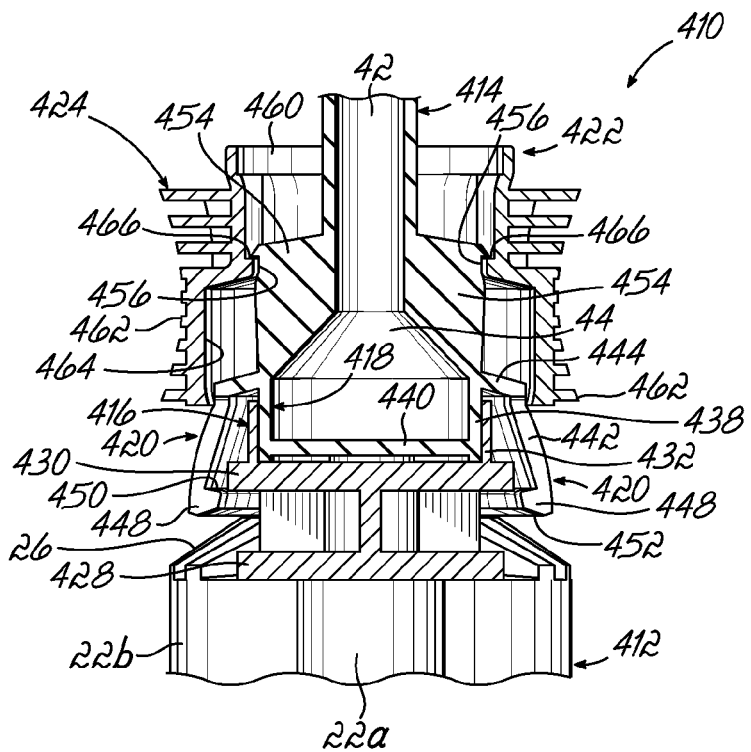
FIG. 26A is a partially cross-sectioned side view of the dispensing assembly of FIG. 25 with the locking ring in the unlocked position.
Figure 26B:
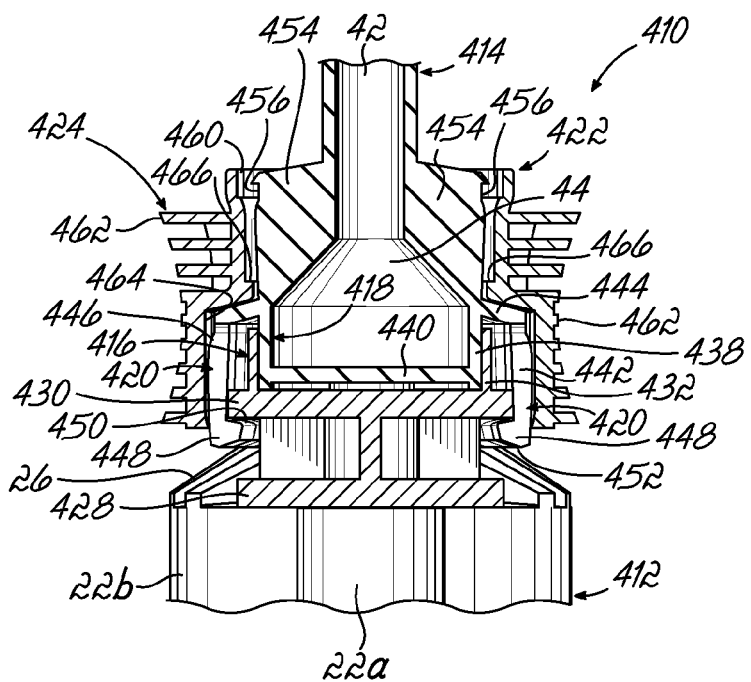
FIG. 26B is a partially cross-sectioned side view of the dispensing assembly of FIG. 25 with the locking ring moved to a locked position.

The fluid in the cartridge 412 may then be dispensed through the mixer conduit 42 and the dispensing outlet 50. When the mixing and dispensing operation is completed, the mixer 414 may be removed from the cartridge 412 in a snap-off process. More specifically, from the position shown in FIG. 26B, a user applies manual pressure on the gripping surfaces 462 to slide the locking ring 424 back to the unlocked position shown in FIG. 26A. In the unlocked position, the locking ring 424 is held on the mixer 414 by the engagement of the locking projection 466 and the locking detents 456 as shown in FIG. 26A. This movement of the locking ring 424 permits the plurality of locking latches 420 to resiliently expand back outwardly to a rest position in which the locking tabs 448 are disengaged from the second proximal wall 430. From the position shown in FIG. 26A, the user can then freely pull the mixer 414 and the inlet socket 418 away from the outlet socket 416 of the cartridge 412, back to the disengaged position. As with the connection process, the disconnection of the mixer 414 from the cartridge 412 requires no relative rotation of these components and therefore reduces or eliminates the likelihood of cross contamination of fluids. Furthermore, the movement of the locking ring 424 between locked and unlocked positions may be performed in a quick and easy manner, thereby reducing the amount of time necessary to assemble and disassemble the dispensing assembly 410.

While the present invention has been illustrated by a description of several embodiments, and while such embodiments have been described in considerable detail, there is no intention to restrict, or in any way limit, the scope of the appended claims to such detail. Additional advantages and modifications will readily appear to those skilled in the art. For example, the peel handle and/or locking ring features described in association with the mixers of several embodiments may be incorporated on the cartridge in other embodiments consistent with the invention. In another alternative, any number of squeeze handles or peel handles may be provided on the locking latches of the various embodiments disclosed herein, such as a mixer including two locking latches with two peel handles. Therefore, the invention in its broadest aspects is not limited to the specific details shown and described. The various features disclosed herein may be used in any combination necessary or desired for a particular application. Consequently, departures may be made from the details described herein without departing from the spirit and scope of the claims which follow.

What is claimed is:

1. A dispensing assembly, comprising:
a cartridge for containing a fluid, said cartridge including a fluid chamber and an outlet socket in communication with said fluid chamber, said outlet socket defining a proximal wall and a hollow port extending distally from said proximal wall;
a mixer for mixing and dispensing the fluid, said mixer including a mixer conduit, an inlet socket sized to be engaged with said hollow port and in fluid communication with said mixer conduit, and a first locking latch extending outwardly from said inlet socket and configured to snap into engagement with said proximal wall to couple said cartridge to said mixer, wherein said first locking latch is integrally molded with said mixer conduit and said inlet socket to provide said mixer as a unitary piece; and
a latch release mechanism coupled to said first locking latch and operable to disengage said first locking latch from said proximal wall without rotating said mixer with respect to said cartridge, wherein said latch release mechanism includes a first squeeze handle extending distally from said first locking latch towards said mixer conduit, said first squeeze handle configured to be depressed towards said mixer conduit to snap said first locking latch out of engagement with said proximal wall,
wherein said mixer further includes a second locking latch positioned on an opposite side of said inlet socket from said first locking latch, and said latch release mechanism includes a second squeeze handle coupled to said second locking latch and extending distally from said second locking latch towards said mixer conduit,
wherein one of said outlet socket and said inlet socket includes a radial projection and the other of said outlet socket and said inlet socket includes a radial slot for receiving said radial projection when said cartridge and said mixer are coupled together by snapping said first locking latch into engagement with said proximal wall, wherein said radial projection and said radial slot prevent any rotation of said mixer relative to said cartridge while said mixer and said cartridge are coupled together, and
wherein said inlet socket of said mixer defines an outer periphery provided by an uninterrupted 360° annular wall, and the only structure projecting outwardly beyond said outer periphery consists of said radial projection, said first and second locking latches, and said first and second squeeze handles.

2. The dispensing assembly of claim 1, wherein said outlet socket includes first and second fluid outlets having different sizes, said inlet socket includes first and second fluid inlets corresponding to said first and second fluid outlets, and said first locking latch and said radial projection are arranged collectively in a non-symmetrical arrangement to align said fluid outlets and said fluid inlets when said cartridge and said mixer are coupled together.

3. The dispensing assembly of claim 1, wherein said outlet socket includes first and second fluid outlets having different sizes, said inlet socket includes first and second fluid inlets corresponding to said first and second fluid outlets, and said first and second locking latches are arranged collectively in a non-symmetrical arrangement to align said fluid outlets and said fluid inlets when said cartridge and said mixer are coupled together, the non-symmetrical arrangement being defined by said first and second locking latches being offset from a central axis or axis of symmetry defined through said mixer along a longitudinal length thereof.

4. A dispensing assembly, comprising:
a cartridge for containing a fluid, said cartridge including a fluid chamber and an outlet socket in communication with said fluid chamber, said outlet socket defining a proximal wall and a hollow port extending distally from said proximal wall;
a mixer for mixing and dispensing the fluid, said mixer including a mixer conduit, an inlet socket sized to be engaged with said hollow port and in fluid communication with said mixer conduit, and a first locking latch extending outwardly from said inlet socket and configured to snap into engagement with said proximal wall to couple said cartridge to said mixer, wherein said first locking latch is integrally molded with said mixer conduit and said inlet socket to provide said mixer as a unitary piece; and
a latch release mechanism coupled to said first locking latch and operable to disengage said first locking latch from said proximal wall without rotating said mixer with respect to said cartridge, wherein said latch release mechanism includes a first squeeze handle extending distally from said first locking latch towards said mixer conduit, said first squeeze handle configured to be depressed towards said mixer conduit to snap said first locking latch out of engagement with said proximal wall,
wherein said mixer further includes a second locking latch positioned on an opposite side of said inlet socket from said first locking latch, and said latch release mechanism includes a second squeeze handle coupled to said second locking latch and extending distally from said second locking latch towards said mixer conduit,
wherein one of said outlet socket and said inlet socket includes a radial projection and the other of said outlet socket and said inlet socket includes a radial slot for receiving said radial projection when said cartridge and said mixer are coupled together by snapping said first locking latch into engagement with said proximal wall, wherein said radial projection and said radial slot prevent any rotation of said mixer relative to said cartridge while said mixer and said cartridge are coupled together,
wherein said latch release mechanism further includes a locking ring engaged with said first and second locking latches, said locking ring moveable along said first and second locking latches from a locked position to an unlocked position, wherein said locking ring in the locked position compresses said first and second locking latches to prevent disengagement from said proximal wall,
wherein said first and second locking latches include retention projections at the locked and unlocked positions, and said locking ring includes corresponding detents for engaging said retention projections to hold said locking ring in the locked position or the unlocked position, and
wherein each of said first and second locking latches include a base connected to and extending outwardly from said inlet socket and an arm spaced apart from said inlet socket and extending proximally in an opposite direction relative to said base from said corresponding first or second squeeze handle, such that said arm and said corresponding first or second squeeze handle are extending on opposite sides of said base, said locking ring moving along said first and second locking latches between said retention projections without contacting said first and second squeeze handles.

5. The dispensing assembly of claim 4, wherein said first and second locking latches are formed so as to be biased away from said proximal wall when said locking ring is moved to the unlocked position, thereby automatically disengaging said first and second locking latches from said proximal wall.

6. The dispensing assembly of claim 1, further comprising:
a sealing cap configured to engage said cartridge to close said outlet socket when said mixer is disengaged from said cartridge, said sealing cap including first and second locking latches configured to snap into engagement with said proximal wall and first and second squeeze handles coupled to said first and second locking latches and configured to be depressed towards one another to snap said first and second locking latches out of engagement with said proximal wall.

7. The dispensing assembly of claim 6, wherein said sealing cap includes a blocking member coupled to said first and second squeeze handles and located between said first and second squeeze handles to prevent unintentional depression of said first and second squeeze handles until said blocking member is removed from said sealing cap.

8. The dispensing assembly of claim 1, further comprising:
a sealing cap configured to engage said cartridge to close said outlet socket when said mixer is disengaged from said cartridge, said sealing cap including a first locking latch configured to snap into engagement with said proximal wall and first and second squeeze handles, one of which is coupled to said first locking latch, wherein said first and second squeeze handles are configured to be depressed towards one another to snap said first locking latch out of engagement with said proximal wall.

9. The dispensing assembly of claim 1, wherein said outlet socket includes a generally annular wall interrupted by a locking notch, said first locking latch includes a base extending radially outwardly from said inlet socket and an arm coupled to said base for snapping into engagement with said proximal wall, and said base is sized to fit within said locking notch in said outlet socket.

10. The dispensing assembly of claim 9, wherein said locking notch includes a ramp surface, said arm includes a locking tab with a leading surface that is chamfered or rounded, and said ramp surface and said leading surface cooperate to assist with snapping said first locking latch into engagement with said proximal wall.

11. A mixer configured to receive and dispense a fluid from a cartridge containing the fluid and including an outlet socket with a proximal wall and a hollow port including a radial slot, the mixer comprising:

a mixer conduit;
an inlet socket in fluid communication with said mixer conduit and sized to be engaged with the hollow port of the outlet socket of the cartridge;
a first locking latch extending outwardly from said inlet socket and configured to snap into engagement with the proximal wall of the cartridge to couple the mixer to the cartridge, wherein said first locking latch is integrally molded with said mixer conduit and said inlet socket to provide the mixer as a unitary piece;
a second locking latch positioned on an opposite side of said inlet socket from said first locking latch;
a latch release mechanism coupled to said first locking latch and operable to disengage said first locking latch from the proximal wall without rotating the mixer with respect to the cartridge, wherein said latch release mechanism includes a first squeeze handle extending distally from said first locking latch towards said mixer conduit, said first squeeze handle configured to be depressed towards said mixer conduit to snap said first locking latch out of engagement with the proximal wall, and said latch release mechanism includes a second squeeze handle coupled to said second locking latch and extending distally from said second locking latch towards said mixer conduit; and
a radial projection extending outwardly from said inlet socket, the radial projection sized to be received in the radial slot to prevent any rotation of the mixer relative to the cartridge while the mixer and the cartridge are coupled together,
wherein said inlet socket defines an outer periphery provided by an uninterrupted 360° annular wall, and the only structure projecting outwardly beyond said outer periphery consists of said radial projection, said first and second locking latches, and said first and second squeeze handles.

12. The mixer of claim 11, wherein the cartridge includes fluid outlets having different sizes, said inlet socket includes fluid inlets having different sizes, and said radial projection and said first locking latch are arranged collectively in a non-symmetrical arrangement to align said fluid inlets and the fluid outlets when the cartridge is connected to the mixer.

13. A method of mixing and dispensing a fluid contained within a cartridge, the method comprising:
providing the dispensing assembly of claim 1, including the cartridge and the mixer;
connecting the mixer to the cartridge by aligning the inlet socket with the outlet socket;
snapping the first and second locking latches integrally formed with and positioned on the inlet socket into engagement with the proximal wall positioned on the outlet socket to thereby couple the mixer to the cartridge;
dispensing fluid from the fluid chamber through the mixer conduit and out of the mixer;
disengaging the mixer from the cartridge by disengaging the first and second locking latches from the proximal wall without rotating the mixer with respect to the cartridge; and
inserting the radial projection into the radial slot such that the radial projection and radial slot prevent rotation of any portion of the mixer relative to the cartridge while the mixer and the cartridge are coupled together.

14. The method of claim 13, wherein disengaging the mixer from the cartridge further comprises:
depressing the first and second squeeze handles toward each other to force the first and second locking latches to move in an opposite direction away from one another and away from the proximal wall.

15. The method of claim 13, wherein the outlet socket includes fluid outlets having different sizes, the inlet socket includes fluid inlets having different sizes, the radial projection or slot and the first locking latch are collectively arranged in a non-symmetrical arrangement on the inlet socket, and connecting the mixer to the cartridge further comprises:
   automatically coding the fluid outlets and fluid inlets by aligning the non-symmetrical arrangement of the radial projection or slot and the first locking latch with corresponding structure located on the outlet socket.

16. The method of claim 13, further comprising:
   snapping a sealing cap into engagement with the outlet socket of the cartridge after disengaging the mixer from the cartridge, the sealing cap configured to block further flow of the fluid out of the fluid chamber.

17. The method of claim 16, wherein the sealing cap includes first and second squeeze handles, at least one of which is connected to the first locking latch, and a blocking member coupled to the first and second squeeze handles and located between the first and second squeeze handles to prevent unintentional depression of the first and second squeeze handles, and the method further comprises:
   removing the blocking member from engagement with the first and second squeeze handles; and
   depressing the first and second squeeze handles towards one another to snap the first locking latch out of engagement with the proximal wall.

18. The method of claim 13, wherein the outlet socket includes a locking notch with a ramp surface, the first locking latch includes a locking tab with a leading surface that is chamfered or rounded, and snapping the first locking latch into engagement with the proximal wall further comprises:
   engaging and sliding the leading surface of the first locking latch over the ramp surface of the locking notch to guide the first locking latch to snap into engagement with the proximal wall.

* * * * *